US010294531B2

(12) United States Patent
Jewett et al.

(10) Patent No.: US 10,294,531 B2
(45) Date of Patent: May 21, 2019

(54) METHOD, KITS AND MATERIALS FOR DETECTION OF LYME DISEASE *BORRELIA* SP. INFECTION

(71) Applicant: UNIVERSITY OF CENTRAL FLORIDA RESEARCH FOUNDATION, INC., Orlando, FL (US)

(72) Inventors: Mollie Jewett, Orlando, FL (US); Micah Halpern, St. Cloud, FL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 0 days.

(21) Appl. No.: 15/027,862

(22) PCT Filed: Oct. 7, 2014

(86) PCT No.: PCT/US2014/059574
§ 371 (c)(1),
(2) Date: Apr. 7, 2016

(87) PCT Pub. No.: WO2015/054319
PCT Pub. Date: Apr. 16, 2015

(65) Prior Publication Data
US 2016/0237478 A1   Aug. 18, 2016

Related U.S. Application Data

(60) Provisional application No. 61/887,640, filed on Oct. 7, 2013.

(51) Int. Cl.
| *G01N 1/40* | (2006.01) |
| *C07K 14/20* | (2006.01) |
| *C12Q 1/689* | (2018.01) |
| *C12Q 1/6804* | (2018.01) |
| *G01N 33/569* | (2006.01) |

(52) U.S. Cl.
CPC .............. *C12Q 1/689* (2013.01); *C07K 14/20* (2013.01); *C12Q 1/6804* (2013.01); *G01N 33/56911* (2013.01); *C07K 2319/40* (2013.01); *G01N 2001/4038* (2013.01); *G01N 2333/20* (2013.01); *G01N 2458/10* (2013.01); *G01N 2469/20* (2013.01)

(58) Field of Classification Search
None
See application file for complete search history.

(56) References Cited

U.S. PATENT DOCUMENTS

| 2006/0147906 A1* | 7/2006 | Zwerschke ......... C07K 14/005 435/5 |
| 2012/0135072 A1 | 5/2012 | Levet et al. |
| 2012/0142023 A1 | 6/2012 | Ascoli et al. |
| 2013/0115634 A1 | 5/2013 | Meura et al. |

OTHER PUBLICATIONS

Niemeyer (TRENDS in Biotechnology (2005) vol. 23, pp. 208-216).*
Editorial (Nature reviews Microbiology (2011) vol. 9, p. 628).*
McKie (Journal of Immunological Methods (2002) vol. 270, pp. 135-141).*
Burbelo ( Clinical and Vaccine Immunology (2010) vol. 17, pp. 904-909).*
Hellwage ( The Journal of Biological Chemistry (2001) vol. 276, pp. 8427-8435).*
Schulte-Spechtel ( International Journal of Medical Microbiology (2006) vol. 296 S1, pp. 250-266).*
Halpern et al., "Enhanced detection of host response antibodies to Borrelia burgdorferi using immuno-PCR", Clinical and Vaccine Immunology, Mar. 2013, vol. 20, No. 3, pp. 350-357.
Panelius et al., "Diagnosis of Lyme neuoborreliosis with antibodies to recombinant proteins DbpA, BBK32 and OspC, and V1sE IR6 peptide", Journal of Neurology, 2003, vol. 250, No. 11, pp. 1318-1327.
Aguero-Rosenfeld, et al., "Diagnosis of Lyme Borreliosis", Clinical Microbiology Reviews, Jul. 2005, vol. 18, No. 3, pp. 484-509.
Barbour, A.G.et al., "A Genome-Wide Proteome Array Reveals a Limited Stet of Immunogens in Natural Infections of Humans and Whit-Footed Mice with Borrelia burgdorferi", Infection and Immunity, Aug. 2008, vol. 76, No. 8, pp. 3374-3389.
Brissette, C.A. et al., "The Borrelial Fibronectin-Binding Protein RevA is an Early Antigen of Human Lyme Disease", Clinical and Vaccine Immunology, Feb. 2010, vol. 17, No. 2, pp. 274-280.
Burbelo, P.D. et al., "Rapid, Simple, Quantitative and Highly Sensitive Antibody Detection for Lyme Disease", Clinical and Vaccine Immunology, Jun. 2010, vol. 17, No. 6, pp. 904-909.
Coleman, A.S. et al., "BBK07 Immunodominant Peptides as Serodiagnostic Markers of Lyme Disease", Clinical and Vaccine Immunology, Mar. 2011, vol. 18, No. 3, pp. 406-413.

(Continued)

*Primary Examiner* — Steven Pohnert
(74) *Attorney, Agent, or Firm* — Timothy H. Van Dyke; Beusse, Wolter, Sanks & Maire PLLC

(57) ABSTRACT

Disclosed herein are method, materials and kits for detection of *B. Burgdorferi* infection or determining stage of Lyme disease in a subject. Exemplified is a method of diagnosing an infection in a subject, the method involving exposing a biological sample from the subject to a capture substrate under conditions for an infection marker in said biological sample to associate with the capture substrate to form a capture complex; associating said capture complex with a marker complex, said marker complex comprising an oligonucleotide; and amplifying said oligonucleotide of marker complex associated with said capture complex to produce an amplification signal; wherein an amplification signal above a predetermined signal threshold indicates that said subject is infected.

9 Claims, 17 Drawing Sheets

Specification includes a Sequence Listing.

(56) References Cited

OTHER PUBLICATIONS

Crother, T.R. et al., "Temporal Analysis of the Antigenic Composition of Borrelia burgdorferi during Infection in Rabbit Skin", Infection and Immunity, Sep. 2004, vol. 72, No. 9, pp. 5063-5072.

Feng, S et al., "Humoral Immunity to Borrelia burgdorferi N40 Decorin Binding Proteins during Infection of Laboratory Mice", Infection and Immunity, Jun. 1998, vol. 66, No. 6, pp. 2827-2835.

Halpern, M. et al., "Simple Objective Detection of Human Lyme Disease Infection Using Immuno-PCR and a Single Recombinant Hybrid Antigen", Clinical and Vaccine Immunology, Aug. 2014, vol. 21, No. 8, pp. 1094-1105.

Heikkila, T. et al., "Species-Specific Serodiagnosis of Lyme Arthritis and Neuroborreliosis Due to Borrelia burgdorferi Sensu Stricto, B. afzelii, and B. garinii by Using Decorin Binding Protein A", Journal of Clinical Microbiology, Feb. 2002, vol. 40, No. 2, pp. 453-460.

Kraiczy, P. et al., "Assessment of the regions within complement regulator-acquiring surface protein (CRASP)-2 of Borrelia burgdorferi required for interaction with host immune regulators FHL-1 and factor H", International Journal of Medical Microbiology, 2008, vol. 298, pp. 268-271.

Liang, F.T. et al., "An Immunodominant Conserved Region Within the Variable Domain of V1sE, the Variable Surface Antigen of Borrelia burgdorferi", Journal of Immunology, 1999, vol. 163, pp. 5566-5573.

Nowalk, A.J. et al., "Serologic Proteome Analysis of Borrelia burgdorferi Membrane-Associated Proteins", Infection and Immunity, Jul. 2006, vol. 74, No. 7, pp. 3864-3873.

Poljak, A. et al., "Identification and characterization of Borrelia antigens as potential vaccine candidates against Lyme borreliosis", Vaccine, 2012, vol. 30, pp. 4398-4406.

Roessler, D. et al., "Heterogeneity of BmpA (P39) among European Isolates of Borrelia burgdorferi Sensu Lato and Influence of Interspecies Variability on Serodiagnosis", Journal of Clinical Microbiology, Nov. 1997, vol. 35, No. 11, pp. 2752-2758.

Schwartz, I. et al., "Polymer Chain Reaction Amplification of Culture Supernatants for Rapid Detection of Borrelia burgdorferi", Eur J Clin Microbiol Infect Dis, 1993, vol. 12, pp. 879-882.

Wilske, B. et al., "Immunological and Molecular Polymorphisms of OspC, an Immunodominant Major Outer Surface Protein of Borrelia burdorferi", Infection and Immunity, May 1993, vol. 61, No. 5, pp. 2182-2191.

Wormser, G.P. et al., "Yield of Large-Volume Blood Cultures in Patients with Early Lyme Disease", The Journal of Infectious Diseases, 2001, vol. 184, pp. 1070-1072.

Zuckert, W.R., et al., "Comparative Analysis and Immunological Characterization of the Borrelia Bdr Protein Family", Infection and Immunity, Jul. 1999, vol. 67, No. 7, pp. 3257-3266.

* cited by examiner

FIG. 1

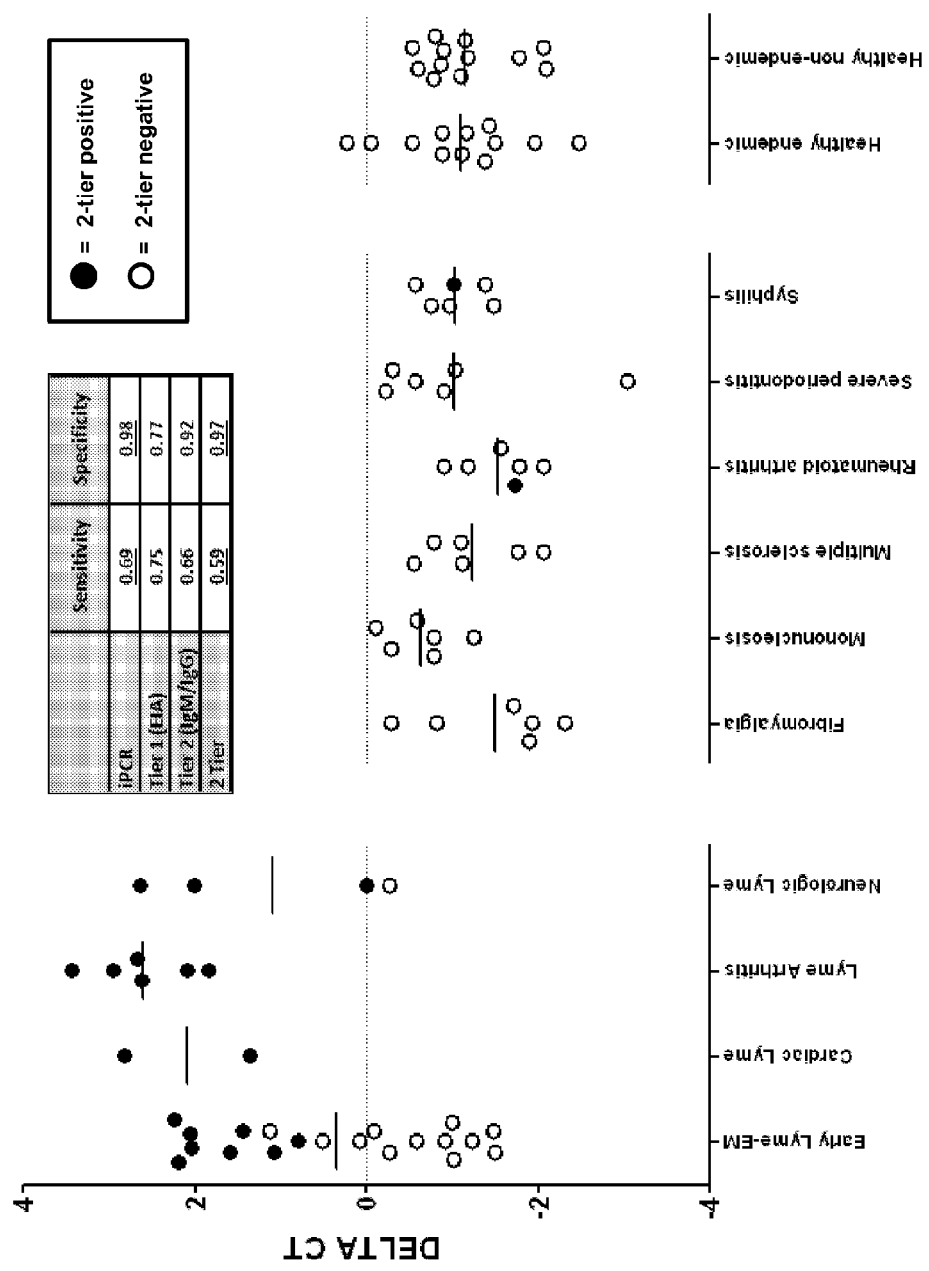
Figure 7. DOC fusion antigen iPCR demonstrates higher sensitivity and specificity compared to 2-tier testing. Early and late stage Lyme, look-alike diseases and healthy individuals. Directly on or above the dotted line indicates iPCR positive.

SEQ ID NO: 1

MIKCNNKTFNNLLKLTILVNLLISCGLTGATKIRLERSAKDITDEIDAIKKDAALKGVNFDAFK
DKKTGSGVSENPFILEAKVRATTVAEKFVIAIEEEATKLKETGSSGEFSAMYDLMFEVSKPL
QKLGIQEMTKTVSDAAEENPPTTAQGVLEIAKKMREKLQRVHTKNYCTLKKKENSTFTDE
KCKNN*PVVAESPKKP*<u>MKKDDQIAAAIALRGMAKDGKFAVK</u>

DbpA

*OspC - PEPC10*

<u>VlsE – C6</u>

BBK19 (SEQ ID NO: 2)

1 mkkyiinlsl clillscnlf skdsrsrqky nfkvpaksvs npinkenidt ekgtnttlci 61 kekdsriiik dcinnqelfk vkskrrydfk kamllgiqta lkvinignnn kkltsikkhn 121 dhillefkdn kiyiirlsel kkhllkskkk pllgspipgg gdaefvddpd grieaeleae 181 qeqemldred fgdeedeele eeifgkekpn n

BBK50 (SEQ ID NO: 3)

| | |
|---|---:|
| LIIKVMLISS LFSSFISCKL YEKLTNKSQQ ALAKAFVYDK DIADNKSTNS | 50 |
| TSKLDNSSLD SIKDNNRSGR TSKALDDAEE IGVKESNQNR NDQQQNNESK | 100 |
| VKESEKNNSS GIQADDSVLD TAHSDASEVE NKKHDTSRQP QLLNKDSSEA | 150 |
| REASKIIQKA STSLEEAEKV NAALKETRSK LDKIKRLADS AKSYLNNARK | 200 |
| NSRTNGSILE ILPNLDKAIE KAISSYASLN VCYTDAIAAL AKAKNDFEHA | 250 |
| KRKANDALEE ALKDIPHFRG YNYLYHYRIN NANDAMESAK SLLEVAKNKQ | 300 |
| KELNENMTKT NKDFQELNDI YKKLQDMDSR | 330 |

Figure 8

FIG. 11A.
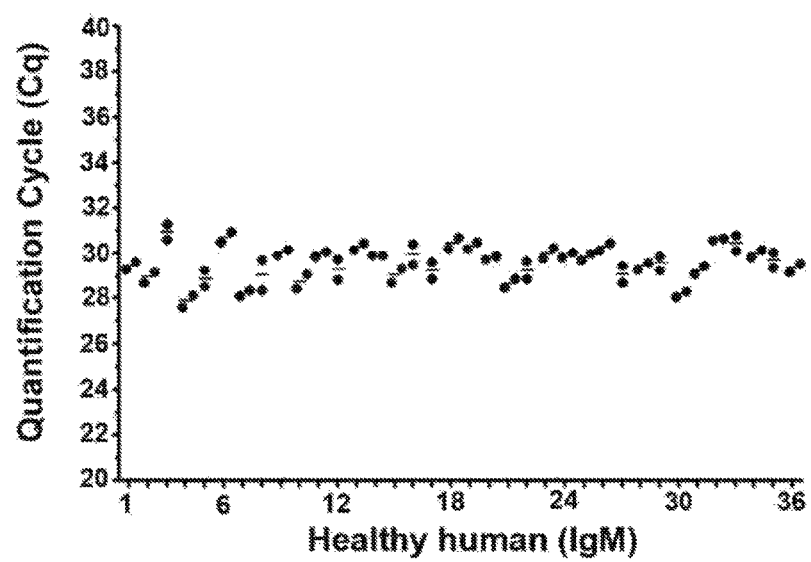
FIG. 11B.
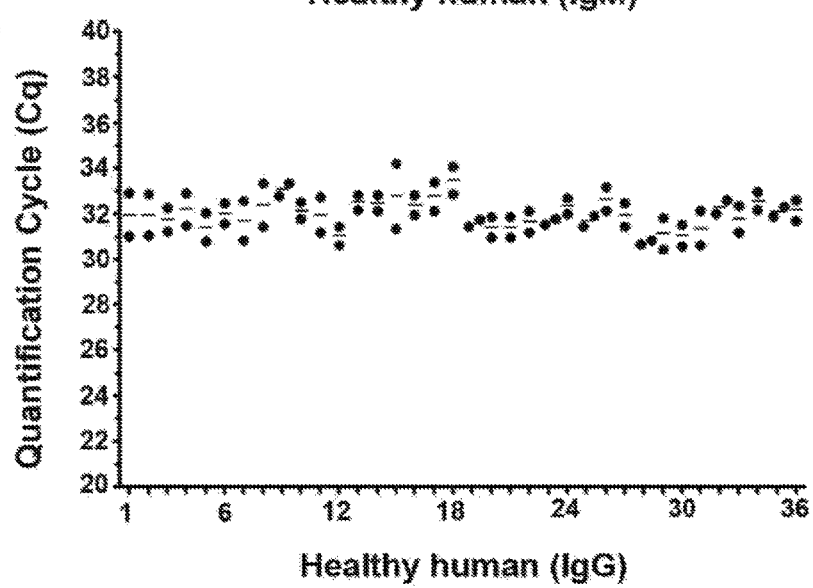
FIG. 11C.
|  | IgM | IgG |
|---|---|---|
| Mean | 29.57 | 32.00 |
| Standard deviation | 0.79 | 0.84 |
| Range | 27.61 - 31.30 | 30.45 - 34.21 |
| Coefficient of variation | 2.66% | 2.63% |

METHOD, KITS AND MATERIALS FOR DETECTION OF LYME DISEASE *BORRELIA* SP. INFECTION

SEQUENCE LISTING

The instant application contains a Sequence Listing which has been submitted electronically in ASCII format and is hereby incorporated by reference in its entirety. Said ASCII copy, created on Dec. 11, 2017, is named 10669-188US_S-L.TXT and is 16,421 bytes in size.

BACKGROUND

Lyme disease caused by infection with the bacterium *Borrelia burgdorferi* has been characterized as the fastest growing zoonotic disease in North America. Accurate diagnosis is currently the greatest challenge for the clinical management of Lyme disease. Current methods for detection of Lyme disease in a clinical setting as approved by the CDC entail a two-tiered approach using a first tier enzyme immunoassay (EIA) followed by a second tier immunoblot for both IgM and IgG *B. burgdorferi* specific antibodies with whole cell *B. burgdorferi* lysates, recombinant antigens or various combinations depending on the commercial kit used. Although adequate, the approach suffers from certain drawbacks including the subjectivity of immunoblot analysis and lack of standardization of antigen source and lysate preparations. These challenges have resulted in discordant results between test strategies for detection of host antibodies based on the kit used largely due to lysate/antigen reagent variability and specificity of the test due to the subjective nature of the analysis. Other methods for detection of Lyme disease include live culture and approaches employing polymerase chain reaction (PCR). Live culture has shown limited success in a clinical setting, is time consuming and requires complex media that has have a limited commercial supply. PCR appears to be the most promising method for direct detection of spirochetes but has not been widely accepted for laboratory diagnosis due to low sensitivity in cerebral spinal fluid and blood and the potential false-positive results due to accidental laboratory contamination of samples with small quantities of target DNA.

BRIEF DESCRIPTION OF DRAWINGS

Figure 1:
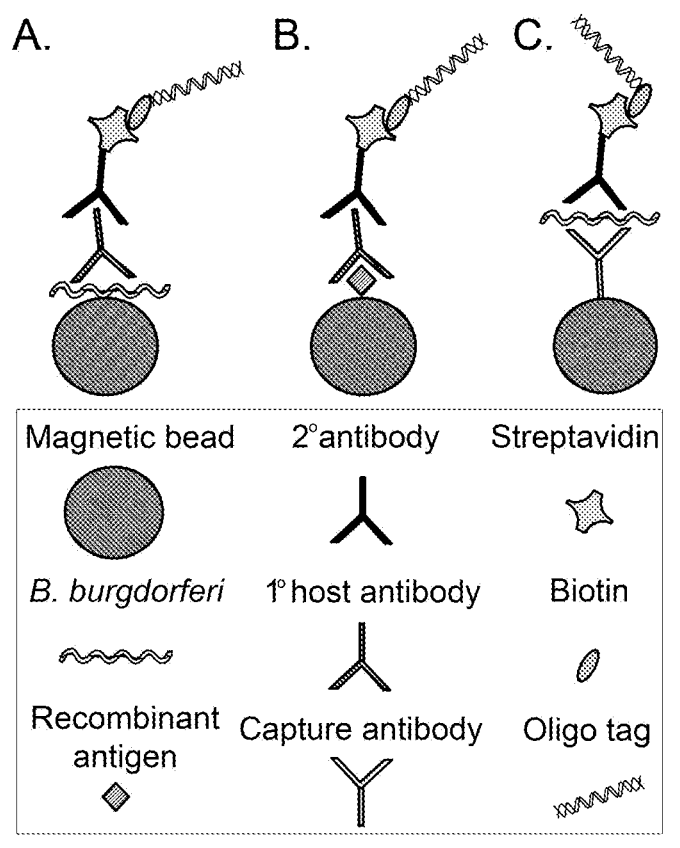

FIG. 1. Schematic representation of immune-PCR (iPCR) assay for detection of Lyme disease biomarkers. (A) Intact spirochete or (B) recombinant protein antigen coupled to magnetic beads was used to capture *B. burgdorferi*-specific host generated antibodies. A biotinylated DNA oligonucleotide reporter molecule coupled to a streptavidin conjugated reporter antibody was amplified by qPCR for detection and quantification. (C) Anti-*B. burgdorferi* antibody coupled to magnetic beads was used for spirochete capture with detection accomplished by qPCR amplification of the DNA oligonucleotide coupled reporter antibody similar to detection of host antibody.

positive, equivocal (equiv) and negative according to the C6 ELISA values. Samples H1-H5 correspond to the sera collected from the healthy controls and are grouped accordingly (healthy). The calculated Spearman rank correlation ($r_s$) was 0.734 (P<0.0001) for C6 iPCR IgM versus C6, 0.826 (P<0.0001) for C6 iPCR IgG versus C6, and 0.895 (P<0.0001) for C6 iPCR IgM and/or IgG versus C6.

Figure 6:
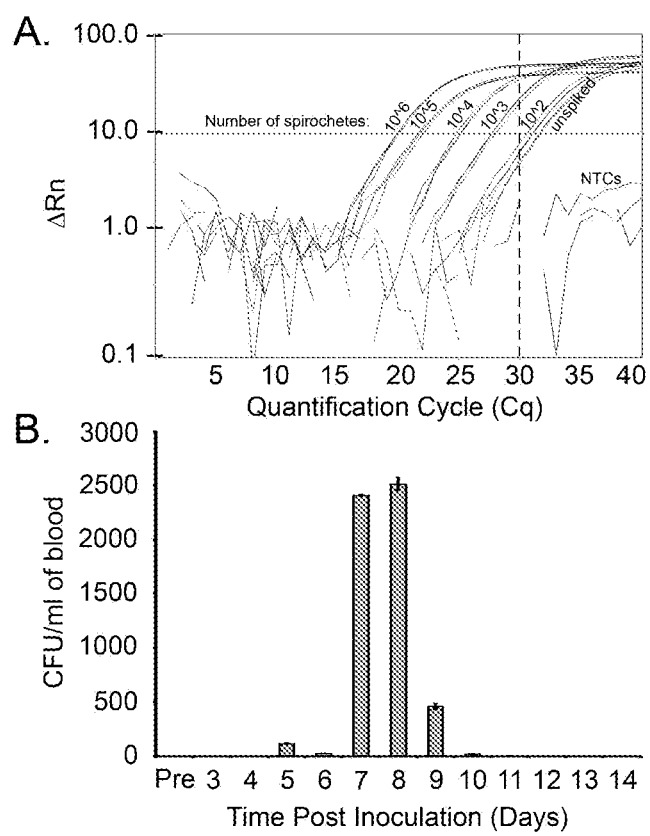

FIG. 6. iPCR has the potential to directly detect *B. burgdorferi* in infected samples. (A) Live spirochetes were serially diluted in HN buffer ($10^6$-$10^2$ spirochetes) and tested in triplicate using iPCR to detect organism capture using anti-*B. burgdorferi* antibody coated magnetic beads. A call threshold was assigned at greater than or equal to five times the standard deviation (Cq=30, vertical broken line) above the mean background signal, as determined using HN buffer alone (unspiked). PCR non-template controls (NTCs) included water and TBST used during the iPCR protocol. (B) Six mice were prebled (pre) and inoculated intradermally with $1\times10^6$ *B. burgdorferi* strain B31 A3. Approximately 50 µl of blood/mouse was collected every day from groups of two mice every three days over a time period of 14 days. Blood collected from each mouse was plated in solid medium using 50 µl of blood and supplemented with a *Borrelia* antibiotic cocktail (see Materials and Methods for details) and the number of colony forming units (cfus) per ml of blood determined. Data shown are the average cfus/ml for the two mice sampled at each time point.

FIG. 7 DOC fusion antigen IPCR demonstrates higher sensitivity and specificity compared to 2-tier testing. A blinded serum panel composed of 92 samples and consisting of Lyme infected individuals both early and late (cardiac, arthritis and neurologic) stage as well as look-alike diseases and healthy individuals from endemic and non-endemic areas were tested in singlet using DOC iPCR for IgG reactivity. Each dot represents a single individual replicate and the horizontal line represents the mean Cq value for all individuals within each category. Filled circles represent samples that were 2-Tier positive with open circles signifying 2-Tier negative status. The y-axis represents the quantification cycle (Cq) determined by real-time PCR. Sensitivity and specificity for iPCR, each tier and combined 2-tier are listed.

FIG. 8 shows a sequence of a hybrid antigen embodiment.

Figure 9:
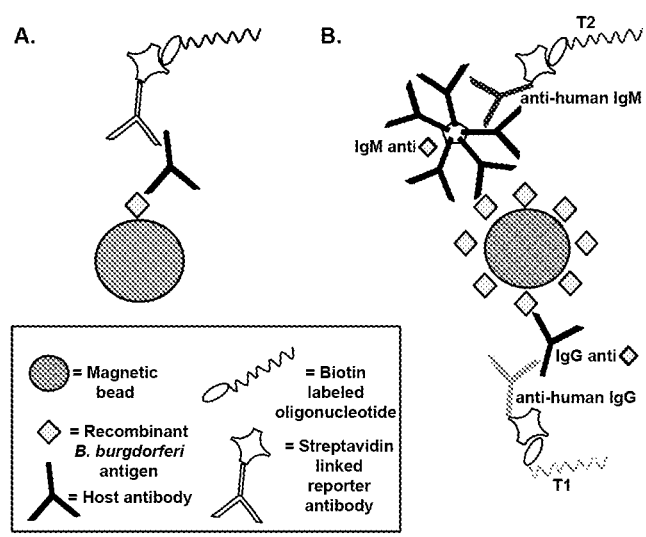

FIG. 9 A schematic representation of the multiplex iPCR assay for detection of Lyme disease host antibodies using recombinant antigens. (A) A recombinant *B. burgdorferi* protein antigen coupled to magnetic beads was used to capture *B. burgdorferi*-specific host-generated antibodies. A biotinylated DNA oligonucleotide reporter molecule coupled to a streptavidin-conjugated reporter antibody was amplified by qPCR for detection and quantification. (B) The same antigen-coupled beads were used to simultaneously capture IgM and IgG host-generated antibodies, which were detected in a multiplex fashion using isotype-specific secondary antibodies coupled to unique reporter oligonucleotides (T1 and T2) similarly amplified by qPCR for detection and quantification.

Figure 10:
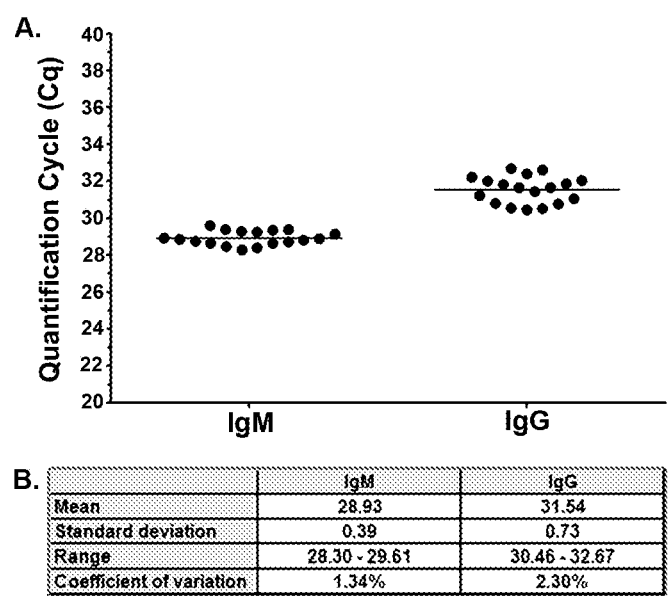

FIG. 10 Lyme disease immuno-PCR magnetic bead protocol demonstrates strong within-assay precision. (A) Serum collected from a single healthy individual was assayed 18 times by IgM/IgG multiplex iPCR using recombinant DbpA antigen coupled to magnetic beads. Each dot represents a single replicate, and the horizontal line represents the mean Cq value for all replicates for each isotype. The y axis represents the quantification cycle (Cq) determined by real-time quantitative PCR. (B) The mean, standard deviation (SD), range, and coefficient of variation (CV) (calculated as the ratio of the SD to the mean) were calculated for both the IgM and IgG Cq values.

FIG. 11 Lyme disease immuno-PCR demonstrates reproducible background across a healthy human population for both IgM and IgG isotypes using the DbpA antigen. Serum samples from 36 healthy individuals were assayed in duplicate by multiplex iPCR using both IgM (A) and IgG (B) secondary antibodies and recombinant DbpA antigen-coupled magnetic beads. Each dot represents a single replicate per individual, with the horizontal lines representing the mean value for duplicate serum samples from each individual. The y axis represents the quantification cycle (Cq) determined by real-time quantitative PCR. (C) The mean, standard deviation (SD), range, and coefficient of variation (CV) (calculated as the ratio of the SD to the mean) is listed for each isotype.

Figure 12:
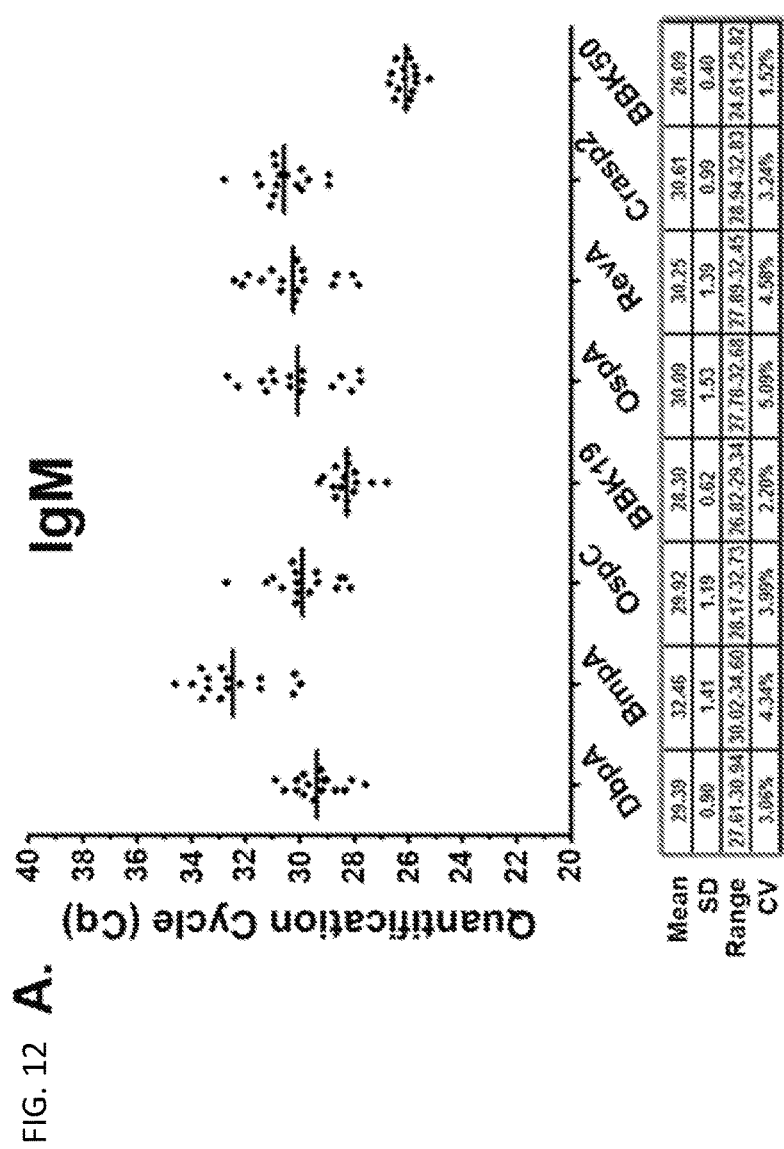
Figure 12:
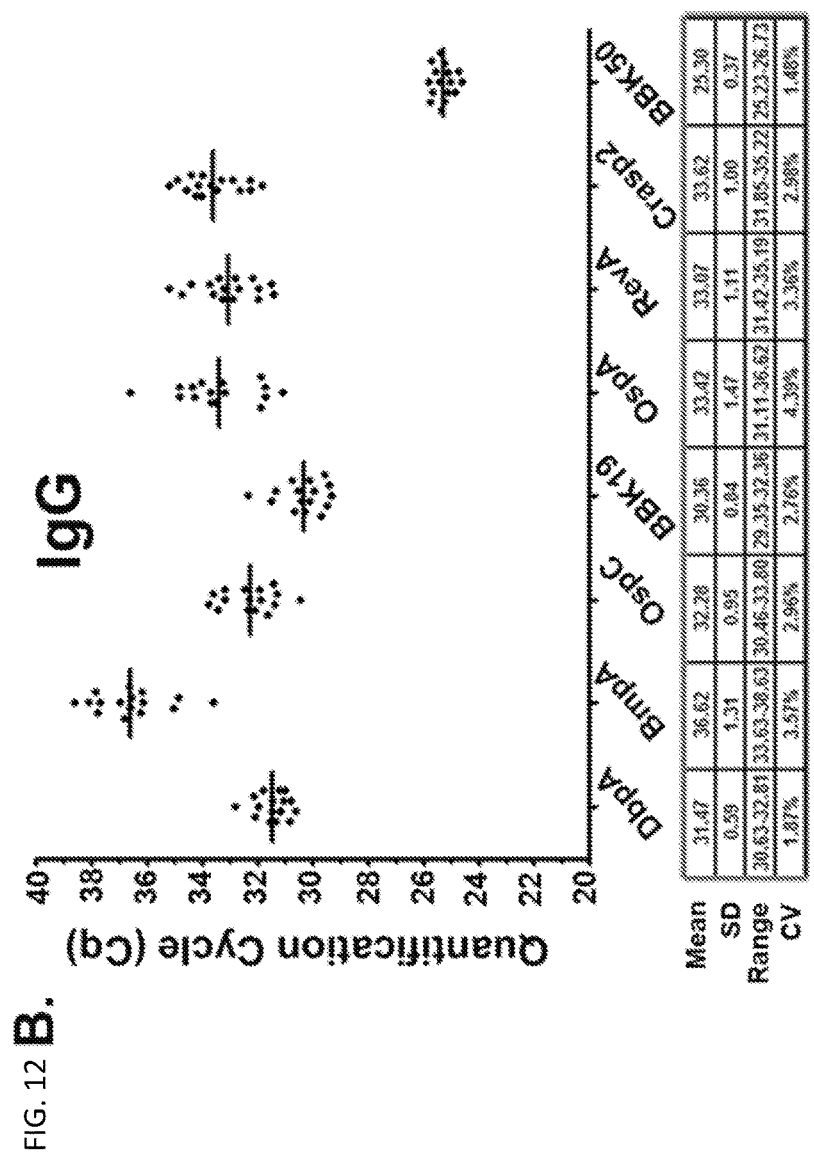

FIG. 12 Immuno-PCR demonstrates low intra-antigen background variability for an antigen panel across a healthy human population. Serum samples from 16 healthy individuals were assayed by multiplex iPCR for both IgM (A) and IgG (B) host-generated antibodies against recombinant DbpA, BmpA, OspC, BBK19, OspA, RevA, Crasp2, and BBK50 antigen-coupled magnetic beads. Each point represents a single individual replicate, and the horizontal lines represent the mean Cq values for all individuals for each antigen/isotype combination. Each antigen mean and standard deviation (SD) value is listed. The y axis represents the quantification cycle (Cq) determined by real-time PCR. The across-population mean, standard deviation, range, and coefficient of variation (CV) values are shown for each antigen/isotype combination.

Figure 13:
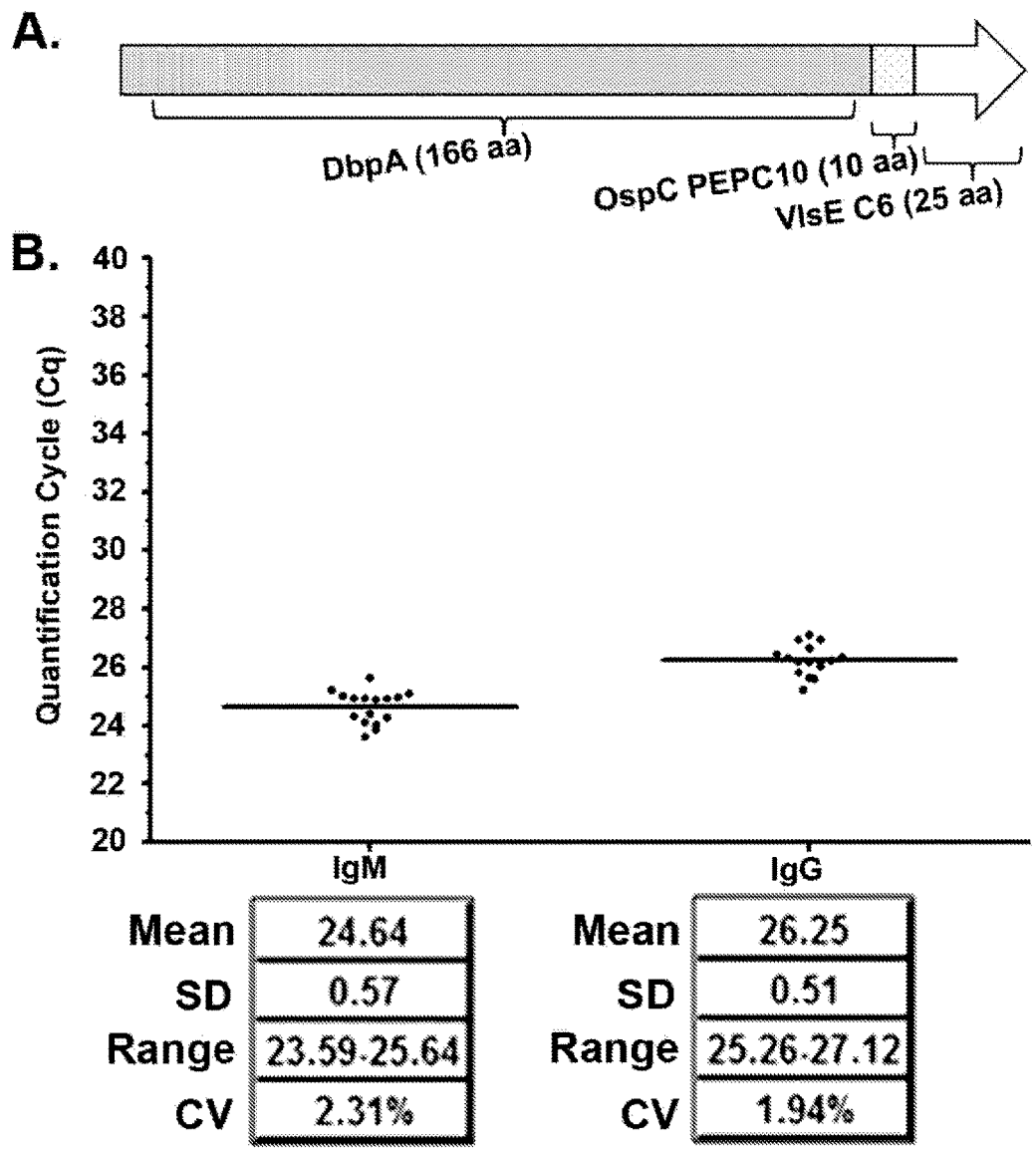

FIG. 13 Development of a hybrid antigen for simple detection of Lyme disease. The DOC antigen was assembled using full-length DbpA protein fused to the PEPC10 (OspC) and the C6 (VIsE) peptides (A) and was tested by iPCR using DOC-coated magnetic beads against 16 healthy individuals for IgM and IgG for the range of the background reactivity (B). (B) Each dot represents a single individual replicate, and the horizontal lines represent the mean Cq values for all individuals for IgM and IgG. The mean, standard deviation (SD), range, and CV values are also listed. The y axis represents the quantification cycle (Cq) determined by real-time quantitative PCR.

FIG. 14 The iPCR assay using the DOC hybrid antigen provides robust detection of Lyme disease. A serum panel composed of 32 samples and consisting of Lyme-infected individuals both early (acute and convalescent) and late (neurologic and arthritis) stage, as well as look-alike diseases and healthy individuals from areas of endemicity and nonendemicity were tested in duplicate using DOC iPCR for both IgG (A) and IgM (B) reactivity. Each dot represents a single individual replicate, and the black horizontal lines represent the mean Cq values for all individuals within each category. The filled circles represent samples that were positive with 2-tier testing, and the open circles signify a 2-tier-negative status. A positive threshold value was established using a multiplier of the standard deviation (SD) above the mean value with the ΔCq threshold (gray horizontal line) representing a value of zero. S1, stage 1; S2, stage 2; S3, stage 3.

Figure 15:
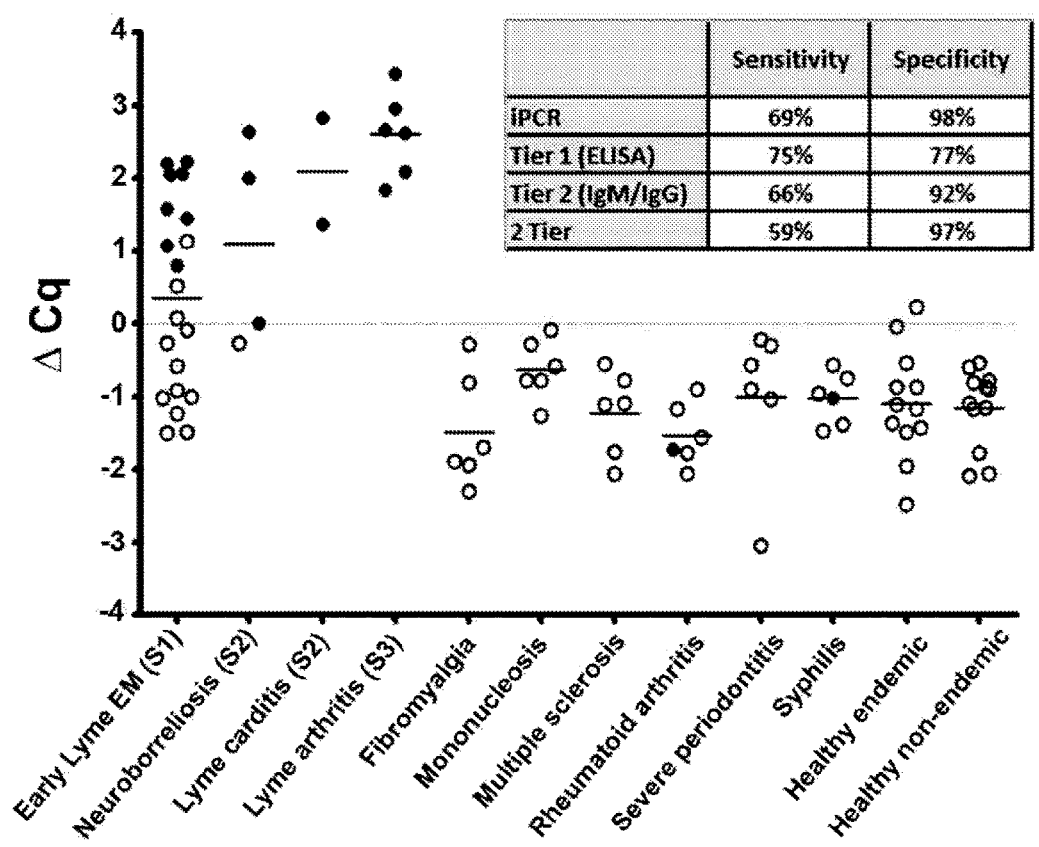

FIG. 15 DOC hybrid antigen IgG iPCR demonstrated sensitive and specific detection of Lyme disease for a blinded serum panel. CDC research panel II was tested in a blinded fashion using DOC iPCR for IgG reactivity. Each dot represents a single individual replicate, and the black horizontal lines represent the mean Cq values for all individuals within each category. The filled circles represent samples that were positive with 2-tier testing, and the open circles signify a 2-tier-negative status. A positive threshold value was established using a multiplier of the standard deviation (SD) above the mean value, with the ΔCq threshold (gray horizontal line) representing a value of zero. The sensitivity and specificity values for iPCR, each tier, and combined 2-tier testing are listed.

Figure 16:
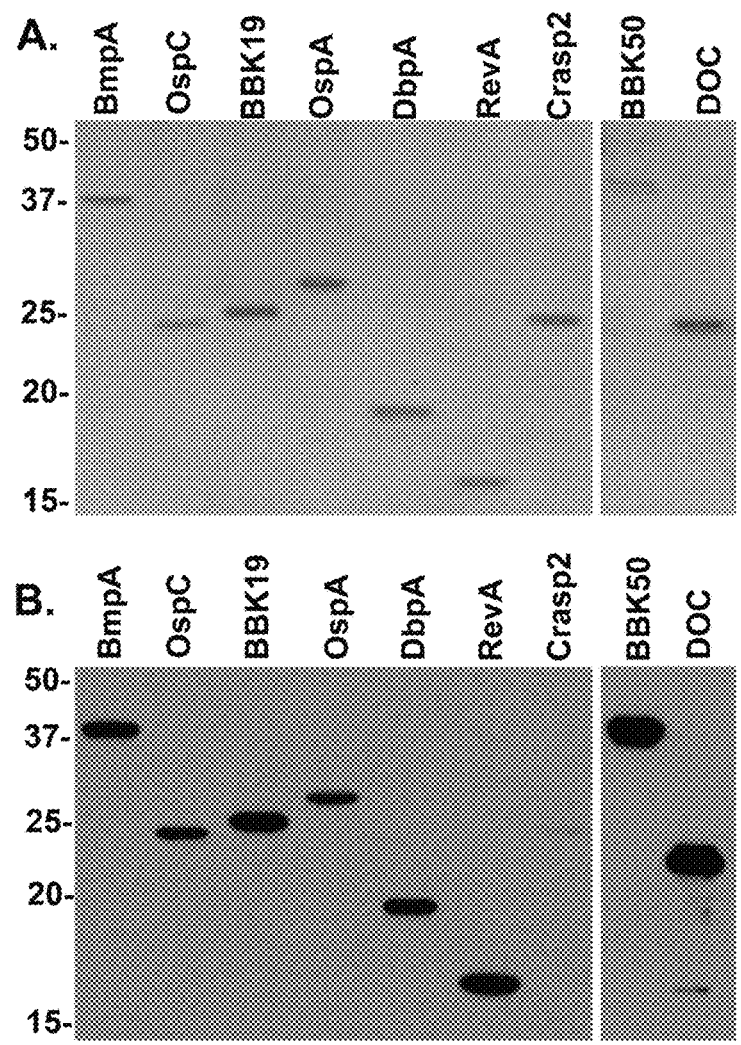

FIG. 16 Purified recombinant protein panel exhibits antigenicity in infected mouse serum. Recombinant proteins expressed in E. coli were protease treated to remove the GST fusion tag followed by subsequent purification to remove residual GST and protease. Purity and seroreactivity was determined by (A) coomassie stained gel and (B) immunoblot using immune serum collected from mice infected with wild-type B. burgdorferi. The positions of markers to the left of the panels depict protein standard molecular masses in kilodaltons.

DETAILED DESCRIPTION

The present disclosure is based on the realization that an improved approach of detecting Lyme disease is needed that utilizes the sensitivity of PCR combined with a detection strategy using a limited number of antigens for determination of host response antibodies. Disclosed herein are embodiments of an approach that utilize immuno-PCR (iPCR), and, optionally, employ a single hybrid recombinant antigen that combines three highly antigenic in vivo-expressed B. burgdorferi antigens for objective highly sensitive and specific detection of a host immune response to B. burgdorferi infection. The hybrid recombinant antigen designated 'DOC' consists of full length DbpA protein fused to the C6 peptide of VlsE and the PEP10 peptide of OspC.

The terminology used herein is for the purpose of describing particular embodiments only and is not intended to be limiting. As used herein, the singular forms "a," "an," and "the" are intended to include the plural forms as well, unless the context clearly indicates otherwise these terms do not denote a limitation of quantity, but rather denote the presence of at least one of the referenced item. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order, quantity or importance, but rather the terms first, second, etc., are used to distinguish one element from another.

One embodiment of the iPCR method disclosed includes aspects of a liquid-phase protein detection method that combines the sensitivity of PCR with the specificity and versatility of immunoassay-based protocols. By combining the iPCR approach with a single hybrid antigen, a number of the issues posed to Lyme disease diagnostics are alleviated. One of the approaches described herein provides a single streamlined quantitative test that provides equivalent sensitivity and increased specificity compared to existing two-tier testing. iPCR combined with the DOC recombinant antigen only required testing of the IgG antibody fraction for a positive diagnosis and appears to have the potential to determine both the stage and type of disease (arthritis, carditis, neurological, etc). Approaches disclosed reduce the cost and complexity of current testing and more importantly provides a means of reagent standardization that has proven to be difficult for many of the existing commercial assays. The combination of the iPCR method with a single hybrid recombinant B. burgdorferi antigen provides a novel method for detection of Lyme disease.

In one embodiment, disclosed is a method of diagnosing an infection in a subject. This method embodiment involves exposing a biological sample from the subject to a capture substrate under conditions for an infection marker in said biological sample to associate with the capture substrate to form a capture complex. The method then involves associating the capture complex with a marker complex, wherein the marker complex includes an oligonucleotide; and amplifying the oligonucleotide of the marker complex associated with the capture complex to produce an amplification signal. If the amplification signal is at a given threshold complex then this is indicative of an infection.

In a more specific embodiment, the capture substrate used in the disclosed method embodiments includes a solid support. Examples of solid supports include but are not limited to a surface of a bigger structure such as wells in a well plate or may pertain to a bead or pellet. In an even more specific example, the solid support is a magnetic bead.

Infections that may be detected by the disclosed method embodiments includes but is not limited to, parasites, bacteria, viruses, or fungi. In a specific embodiment, the infection detected is a bacterial infection by a Lyme disease Borrelia species. The Lyme disease Borrelia species is Borrelia burgdorferi, Borrelia afzelli and/or Borrelia garinii.

In another embodiment, the capture substrate used in the disclosed method embodiments involves an antigen linked to a solid support. In a more specific embodiment, the antigen is a recombinant antigen. In an even more specific embodiment, the recombinant antigen has an epitope of a Borrelia species (e.g. B. burgdorferi, Borrelia afzelli and/or Borrelia garinii).

In addition, the aforementioned recombinant antigen may include a protein, or portion thereof, having a sequence derived from a Borrelia species. Examples of recombinant antigens may include but are not limited to full length sequences or portions of the OspC, BmpA, VlsE, DbpA, BBK19, OspA, RevA, Crasp2, or BBK50, or portions of the foregoing, or combinations or fusions of the foregoing proteins, or combinations or fusions of the foregoing.

Recombinant antigens may also include a tag. Examples of useful tags include but are not limited to a glutathione-S-transferase (GST) tag, a hemagglutinin, or C-Myc, or combinations thereof. Typically, the tags are used to assist in purification of the recombinant antigen after expression and are cleaved prior to implementation in the assay methods. Accordingly, in specific embodiments, recombinant antigens useful in the disclosed method embodiments include GST-OspC, GST-BmpA, or GST-VlsE (C6), or combinations thereof.

Another embodiment involves a recombinant antigen that includes a fusion protein of (i) full length DbpA; (ii); OspC (PEP10) and (iii) VlsE (C6). In frame glutathione-S-transferase (GST) fusion protein for the DOC hybrid protein was generated using two distinct PCR amplification steps. First, the corresponding coding regions for DbpA and C6 were amplified separately from B. burgdorferi genomic DNA with non-template addition of the PEPC10 sequence to each amplicon using primer pairs P17 and P18 (DbpA-PEPC10) and P19 and P20 (C6-PEPC10) engineered with BamHI/SalI restriction sites (Table 1). Both PCR products were diluted 100-fold, combined and synthetically assembled into the DOC construct by overlapping PCR using primer pairs P17 and P20. Final constructs were sequenced verified and recombinant protein generated and purified as described for previous antigens.

In a further embodiment, the aforementioned capture substrate pertains to an antibody linked to a solid support wherein the antibody binds to a Lyme disease *Borrelia* species organism or a Lyme disease *Borrelia* species antigen.

In another embodiment, an infection marker typically captured during the method embodiments is a primary host antibody that binds to a Lyme disease *Borrelia* species or a Lyme disease *Borrelia* epitope comprising antigen.

According to alternative embodiment, the capture substrate involves whole organism associated with a solid substrate.

An example of a marker complex useful in the method embodiments includes but is not limited to a marker antibody associated with said oligonucleotide. The marker antibody typically binds to a primary host antibody that binds to a Lyme disease *Borrelia* species or a Lyme disease *Borrelia* epitope comprising antigen. In a more specific example, the marker complex may include a linker between the associated oligonucleotide and the marker antibody. One non-limiting example of a linker includes biotin and streptavidin. Other linkers may include, but are not limited to, peptides and polyethers, and the like, which can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Examples of biological samples typically obtained for use in certain method embodiments include but are not limited to a fluid, cell, stool sample, tissue, or tissue lysate obtained from the subject. Examples of fluids include but are not limited blood, serum, semen, urine, saliva, tears, perspiration, breath condensate, or vaginal fluid, cerebral spinal fluid, epithelial mucus or synovial fluid. Biological samples can be obtained from a subject, which may be a human or non-human mammal.

The amplifying step of the disclosed method embodiments typically involves the implementation of a polymerase chain reaction (PCR). For example, the oligonucleotide of the marker complex associated with the capture complex is amplified by PCR. A signal relating to the amount of amplified oligonucleotide is the amplified signal. Positive threshold values were established for each individual antigen using an antigen specific multiplier of the standard deviation (SD) above the mean value for a group of sixteen healthy individuals. The antigen specific multiplier was determined using a panel of samples from Lyme disease patients, patients with Lyme disease look-alike diseases and healthy individuals and set at a minimal value where all culture positive individuals resulted in a positive delta Cq above background In a further embodiment of a capture substrate useful in the infection detection methods includes a solid support associated with a microbe organism. Examples of the microbe organism include but are not limited to parasites, bacteria, viruses or fungi.

According to another embodiment, disclosed is a recombinant antigen comprising a fusion protein of (i) full length DbpA; (ii) OspC (PEP10); and (iii) VlsE (C6).

In yet a further embodiment, disclosed is a capture substrate comprising a solid support linked with a recombinant antigen comprising a fusion protein of (i) full length DbpA; (ii) OspC (PEP10); and (iii) VlsE (C6) or a bacterial sample of a Lyme disease *Borrelia* species.

Another embodiment involves a kit for detecting an infection is a subject. The kit may include:

(a) a composition comprising a capture substrate that comprises a solid support linked with (i) a recombinant antigen comprising an epitope of a Lyme disease *Borrelia* species, (ii) a solid support linked with a bacterial sample of a Lyme disease *Borrelia* species; or (iii) a solid support linked with an antibody that binds to a Lyme disease *Borrelia* species or Lyme disease *Borrelia* species antigen; and (b) a composition comprising a marker complex comprising a marker antibody associated with an oligonucleotide, wherein the marker antibody binds to a primary host antibody that binds to a Lyme disease *Borrelia* species or a Lyme disease *Borrelia* epitope comprising antigen.

Alternatively or additionally, the kits can include one or more isolated primers or primer pairs for amplifying the oligonucleotide of the marker complex.

The kit may further include one or more of a buffer solution, a conjugating solution for developing the signal of interest, or a detection reagent for detecting the signal of interest, each in separate packaging, such as a container. In another example, the kit includes a plurality of size-associated marker of target nucleic acid sequences for hybridization with a detection array. The kit can also include instructions in a tangible form, such as written instructions or in a computer-readable format.

Kits comprising a primer or probe that is complementary to and specifically hybridizes to or binds to a target genes/mRNA in a sample and enzymes suitable for amplifying target genes/mRNA are provided in certain embodiments of the invention. The primer or probe may be labeled with a radioisotope, a fluorophore, a chromophore, a dye, an enzyme, or TOF carrier. In these kits, binding may be detected by in situ hybridization, PCR RT-PCR, fluorescence resonance energy transfer, chemiluminescence enzymatic signal amplification, electron dense particles magnetic particles and capacitance coupling. The probe is selected to allow the target genes/mRNA to be sequenced if wanted, or for quantitation of the respective different target genes/mRNA as compared to the wild-type sequence. These reagents in certain embodiments may comprise one or more nucleic acid probes, may be in the form of a microarray, are suitable for primer extension and can comprise controls indicative of a healthy individual.

Nucleotides may be amplified to obtain amplification products. Suitable nucleic acid amplification techniques are well known to a person of ordinary skill in the art, and include polymerase chain reaction (PCR) as for example described in Ausubel et al., Current Protocols in Molecular Biology (John Wiley & Sons, Inc. 1994-1998) (and incorporated herein). The most commonly used nucleic acid amplification technique is the polymerase chain reaction (PCR).

PCR is well known in this field and comprehensive description of this type of reaction is provided in E. van Pelt-Verkuil et al., Principles and Technical Aspects of PCR Amplification, Springer, 2008. PCR is a powerful technique that amplifies a target DNA sequence against a background of complex DNA. If RNA is to be amplified (by PCR), it must be first transcribed into cDNA (complementary DNA) using an enzyme called reverse transcriptase. Afterwards, the resulting cDNA is amplified by PCR. PCR is an exponential process that proceeds as long as the conditions for sustaining the reaction are acceptable. The components of the reaction are: i. pair of primers—short single strands of DNA with around 10-30 nucleotides complementary to the regions flanking the target sequence (typically the reporter nucleotide of the marker complex); ii. DNA polymerase—a thermostable enzyme that synthesizes DNA; iii. deoxyribonucleoside triphosphates (dNTPs)—to provide the nucleotides that are incorporated into the newly synthesized DNA strand; and [0027] iv. buffer—to provide the optimal chemical environment for DNA synthesis.

PCR typically involves placing these reactants in a small tube (~10-50 μl) containing the extracted nucleic acids. The tube is placed in a thermal cycler; an instrument that subjects the reaction to a series of different temperatures for varying amounts of time. The standard protocol for each thermal cycle involves a denaturation phase, an annealing phase, and an extension phase. The extension phase is sometimes referred to as the primer extension phase. In addition to such three-step protocols, two-step thermal protocols can be employed, in which the annealing and extension phases are combined. The denaturation phase typically involves raising the temperature of the reaction to 90-95 C to denature the DNA strands; in the annealing phase, the temperature is lowered to ~50-60 C for the primers to anneal; and then in the extension phase the temperature is raised to the optimal DNA polymerase activity temperature of 60-72 C for primer extension. This process is repeated cyclically around 20-40 times.

There are a number of variants to the standard PCR protocol such as multiplex PCR, linker-primed PCR, direct PCR, tandem PCR, real-time PCR and reverse-transcriptase PCR, amongst others, which have been developed for molecular diagnostics.

Multiplex PCR uses multiple primer sets within a single PCR mixture to produce amplicons of varying sizes that are specific to different DNA sequences. By targeting multiple genes at once, additional information may be gained from a single test-run that otherwise would require several experiments. Optimization of multiplex PCR is more difficult though and requires selecting primers with similar annealing temperatures, and amplicons with similar lengths and base composition to ensure the amplification efficiency of each amplicon is equivalent.

Linker-primed PCR, also known as ligation adaptor PCR, is a method used to enable nucleic acid amplification of essentially all DNA sequences in a complex DNA mixture without the need for target-specific primers. The method firstly involves digesting the target DNA population with a suitable restriction endonuclease (enzyme). Double-stranded oligonucleotide linkers (also called adaptors) with a suitable overhanging end are then ligated to the ends of target DNA fragments using a ligase enzyme. Nucleic acid amplification is subsequently performed using oligonucleotide primers which are specific for the linker sequences. In this way, all fragments of the DNA source which are flanked by linker oligonucleotides can be amplified.

Direct PCR describes a system whereby PCR is performed directly on a sample without any, or with minimal, nucleic acid extraction. It has long been accepted that PCR reactions are inhibited by the presence of many components of unpurified biological samples, such as the heme component in blood. Traditionally, PCR has required extensive purification of the target nucleic acid prior to preparation of the reaction mixture. With appropriate changes to the chemistry and sample concentration, however, it is possible to perform PCR with minimal DNA purification, or direct PCR. Adjustments to the PCR chemistry for direct PCR include increased buffer strength, the use of polymerases which have high activity and processivity, and additives Tandem PCR utilizes two distinct rounds of nucleic acid amplification to increase the probability that the correct amplicon is amplified. One form of tandem PCR is nested PCR in which two pairs of PCR primers are used to amplify a single locus in separate rounds of nucleic acid amplification. The first pair of primers hybridize to the nucleic acid sequence at regions external to the target nucleic acid sequence. The second pair of primers (nested primers) used in the second round of amplification bind within the first PCR product and produce a second PCR product containing the target nucleic acid, that will be shorter than the first one. The logic behind this strategy is that if the wrong locus were amplified by mistake during the first round of nucleic acid amplification, the probability is very low that it would also be amplified a second time by a second pair of primers and thus ensures specificity.

Real-time PCR, or quantitative PCR, is used to measure the quantity of a PCR product in real time. By using a fluorophore-containing probe or fluorescent dyes along with a set of standards in the reaction, it is possible to quantitate the starting amount of nucleic acid in the sample. This is particularly useful in molecular diagnostics where treatment options may differ depending on the pathogen load in the sample.

If the reporter nucleotide is an RNA sequence, it can be amplified or converted into cDNA, such as by using RT PCR. Reverse-transcriptase PCR (RT-PCR) is used to amplify DNA from RNA. Reverse transcriptase is an enzyme that reverse transcribes RNA into complementary DNA (cDNA), which is then amplified by PCR. RT-PCR is widely used in expression profiling, to determine the expression of a gene or to identify the sequence of an RNA transcript, including transcription start and termination sites. It is also used to amplify RNA viruses such as human immunodeficiency virus or hepatitis C virus. "cDNA" or "complementary DNA" is DNA synthesized from a messenger RNA (mRNA) template in a reaction catalyzed by the enzyme reverse transcriptase and the enzyme DNA polymerase.

EXAMPLES

Materials and Methods Related to Examples 1-4

Bacterial Strains.

*B. burgdorferi* clone B31 A3 (17) and B31 A34/pBSV2G-loxP-flaBp-gfp (18) were used in these studies. Spirochetes were grown in liquid Barbour-Stoenner-Kelly (BSK) II medium supplemented with gelatin and 6% rabbit serum (19) and plated in solid BSK medium as previously described (20). All spirochete cultures were grown at 35° C. and supplemented with 2.5% $CO_2$. Gentamicin was used at 40 μg/ml. *Escherichia coli* strains DH5α and BL21 (Novagen, Billerica, Mass.) were grown in LB broth, on LB agar plates or in Magic Media (Invitrogen, Carlsbad, Calif.) containing 100 μg/ml ampicillin.

Mouse Infections.

The University of Central Florida (UCF) is accredited by the International Association of Assessment and Accreditation of Laboratory Animal Care. Protocols for all animal experiments were prepared according to the guidelines of the National Institutes of Health and approved by UCF's Institutional Animal Care and Use Committee. For the serological detection experiments, the hair on the upper backs of three mice (C3H/HeN, 6- to 8-week old females; Harlan Laboratories, Inc, Dublin, Va.) was removed by shaving and the mice were needle inoculated intradermally on the upper back with *B. burgdorferi* strain B31 A3 at a dose of 1×10⁵ spirochetes divided between two 50 µl inoculations. The number of spirochetes inoculated into mice was determined using a Petroff-Hausser counting chamber and verified by colony forming units (cfu) counts in solid BSK medium. Total plasmid content of each inoculum was confirmed to be as expected (21). Whole blood samples were collected from the three inoculated mice as well as one non-inoculated mouse by submandibular bleed pre-inoculation and at days 1, 3, 4, 7, 9, 11, 14, 16, 18 and 21 post-infection. The coagulated blood was spun at 4,000×g for 9 minutes to prepare serum. For the spirochete detection experiments, six mice (C3H/HeN, 6-8 week old females, Harlan Laboratories, Inc, Dublin, Va.) were inoculated intradermally with *B. burgdorferi* strain B31 A3 at a dose of 1×10⁵ spirochetes. Approximately 50 µl of blood were collected by submandibular bleed from all mice prior to inoculation. Subsequently, to prevent complications due to oversampling, approximately 50 µl of blood/mouse were collected every day from groups of two mice so that each group of two mice was bled every three days over a time period of 14 days. All blood samples (pre- and post-inoculation) were supplemented with an equal volume of 0.5M sodium EDTA to prevent coagulation. Similar to plating of in vitro grown *B. burgdorferi*, 50 µl of blood from each mouse was combined with BSK plating medium (20) supplemented with a *Borrelia* antibiotic cocktail consisting of 20 µl/ml phosphomycin (MP Biomedicals, Santa Ana, Calif.), 50 µl/ml rifampicin (Fisher Scientific, Waltham, Mass.) and 2.5 µl/ml amphotericin B (Fisher Scientific, Waltham, Mass.), all solubilized in 20% DMSO, poured into sterile petri plates, allowed to solidify and incubated as indicated above for approximately 7 days until *B. burgdorferi* colonies were visible in the solid medium.

Immunoblot and C6 ELISA.

Total *B. burgdorferi* lysate for immunoblot analysis was prepared from a 500 ml culture of 1×10⁸/ml *B. burgdorferi* B31 A3. Spirochetes were harvested by centrifugation and washed two times in 30 ml phosphate buffered saline, pH 7.4 (PBS). Washed cells were resuspended in 30 ml PBS and disrupted by sonication on ice using a Misonix model S-4000 sonciator at 40% amplitude for four repetitions at 20 seconds each. Total protein in the sonicate was normalized to 1 mg/ml with PBS based on absorbance at 280 nm and 75 µg of protein were separated by 12.5% polyacrylamide gel electrophoresis. Following protein transfer, nitrocellulose membranes were incubated for 1 hour with pre- and post-inoculation mouse sera diluted 1:200 in Tris buffered saline/ 0.05% tween, pH 7.6 (TBST), washed twice with TBST, incubated with HRP-conjugated goat anti-mouse IgG/IgM (Chemicon International, Billerica, Mass.) for 1 hour, washed twice with TBST and the signal was detected using the SuperSignal West Pico Chemiluminescent Substrate Kit (Thermo Scientific, Rockford, Ill.). The C6 *B. burgdorferi* ELISA was performed according to manufacturer's protocol (Immunetics, Boston, Mass.) with the exception of the use of HRP-conjugated goat anti-mouse IgG/IgM secondary (Chemicon International, Billerica, Mass.) at a 1:5000 dilution in place of the anti-human reporter antibody provided with the kit when mouse sera were analyzed.

Cloning and Expression of Recombinant GST Tagged Antigens.

In frame glutathione-S-transferase (GST) fusion proteins for OspC, BmpA and the VIsE C6 peptide were generated by PCR amplifying the corresponding coding regions without the signal sequences from *B. burgdorferi* genomic DNA using primer pairs P1 and P2 (OspC), P3 and P4 (BmpA) or P5 and P6 (VIsE C6) engineered with BamHI or SalI restriction sites (Table 1) and Phusion polymerase (New England Biolabs, Ipswich, Mass.). PCR products were purified (Qiagen, Valencia, Calif.), digested with restriction enzymes (New England Biolabs, Ipswich, Mass.) and cloned into BamHI/SalI-digested pGEX-6P-1 (GE Healthcare, Piscataway, N.J.) to generate translational fusions with GST at the N-terminus. Subsequent clones were selected and sequence confirmed by dideoxy sequencing. Hemagglutinin (OspC) and C-Myc (BmpA) tags were included at the C-terminus for determination of protein purity by immunoblot. pGEX-6P-1 plasmids carrying ospC, bmpA or vIsE c6 were transformed into a BL21 strain of *E. coli* (Novagen, Billerica, Mass.). Protein expression and purification were performed according to the procedures outlined in the Bulk GST Purification Module (GE Health Sciences, Piscataway, N.J.).

iPCR Reagent Preparation.

iPCR assays were assembled as two-sided (sandwich) as detailed in FIG. 1 for both host antibody (A and B) and spirochete capture (C). Whole cell lysate used for immunoblot analysis (preparation described above) and GST-fusion recombinant antigens were used to coat magnetic beads for host antibody capture using Dynabeads Antibody Coupling Kit (Invitrogen, Carlsbad, Calif.). Bead coupling reactions were performed overnight according to the manufacturer's protocol using 20-30 µg antigen(s) per mg Dynabeads M-270 Epoxy. The primary antibody used for spirochete capture consisted of protein A purified anti-*B. burgdorferi* polyclonal antibody raised in rabbits against whole cell preparations of *B. burgdorferi* clone B31 ATCC #35210 (Acris Antibodies, San Diego, Calif.) and was coupled to magnetic beads as described above. Protein coated beads were stored at 4° C. The streptavidin conjugated reporter antibodies were prepared using the Lightning-Link Streptavidin Conjugation Kit (Innova Biosciences, Cambridge, United Kingdom) using polyclonal anti-*B. burgdorferi* (Acris Antibodies, San Diego, Calif.), goat anti-mouse IgM/IgG (Sigma-Aldrich, St. Louis, Mo.), goat anti-human IgG (Invitrogen, Carlsbad, Calif.) or goat-anti-human IgM (Invitrogen, Carlsbad, Calif.) according to manufacturer's protocols using an overnight incubation. Following conjugation, 10 µl of streptavidin labeled antibody was diluted 1:50 in TBST and 100 nM of single stranded biotin-labeled oligonucleotide template was added and the mixture rotated at room temperature for 30 minutes for antibody-oligo conjugation. Oligonucleotide sequences T1 (IgG coupled) and T2 (IgM coupled) used for tagging are listed in Table 1. The oligonucleotide linked streptavidin conjugated antibody was then diluted to a 1:100 working stock (1:5000 final dilution) and stored at 4° C.

iPCR Assay.

Following reagent preparation, 10 µl of antigen or antibody coated magnetic beads were incubated in 500 µl TBST for 30 minutes at 25° C. on a rotator. Following preliminary washing, beads were resuspended in 500 µl TBST and 5 µl serum (mouse or human), 10 µl spirochetes suspended in HN buffer or blood (1×10⁸-1×10⁴/ml *B. burgdorferi* B31 A3) or no serum/spirochete (negative control) and incubated at 25° C. rotating for 30 minutes. Beads were subsequently washed and resuspended in 300 µl TBST with the addition of 100 µl each of IgG and IgM diluted (1:5000) biotinylated oligonucleotide streptavidin coupled reporter antibody (anti-mouse IgM/IgG, anti-human IgG, anti-human IgM or anti-*B. burgdorferi*) and incubated at 25° C. rotating for 30 minutes. Following assembly of the immune complex, beads were washed three times with 900 µl TBST followed by magnetic bead capture. Washed immune complex coupled beads were resuspended in 20 µl TBST for subsequent PCR amplification.

Signal Amplification by Real-Time PCR.

To amplify the signal of the immune complex, real-time PCR was performed using an Applied Biosystems 7900 HT (Life Technologies, Grand Island, N.Y.) and IQ Supermix (Bio-Rad, Hercules, Calif.) supplemented with synthetic primers and probes T1F/T1R/T1P (IgG detection) or T2F/T2R/T2P (IgM detection) (Table 1). Duplicate reactions were prepared in 20 µl volumes containing 5 µl of iPCR assay processed beads as template, 10 µl of 2× reaction mix, 0.2 µM each primer and 0.4 µM fluorophore labeled probe. Cycle parameters included a preliminary denaturation (95° C., 20 sec), followed by 40 cycles of denaturation (95° C., 1 sec) and annealing/extension (60° C., 20 sec). The fluorescent signal was collected at the FAM wavelength for IgG reactions and MAX wavelength for IgM reactions. The quantification cycle (Cq) for each reaction was determined using automatic baseline and threshold settings. The average and standard deviation for uninfected/healthy samples were used to determine the background level of amplification as is commonly observed for iPCR protocols. Positive threshold values were established at three times the standard deviation for background levels.

Human Sera.

Retrospective, de-identified human Lyme disease and healthy control serum samples were kindly supplied by Dr. Martin Schriefer (Centers for Disease Control and Prevention, Fort Collins, Colo.). Patient sera were collected from 18 Lyme disease patients from endemic Lyme disease regions upon initial visit to a physician and 10 days post-initial visit (n=36). According to the CDC's 2-tiered serological analysis of the samples, 5 of the patients were 2-tiered positive at both the initial and follow-up time points, 3 of the patients were 2-tiered negative a both time points and 10 of the patients were 2-tiered negative at the initial visit but 2-tiered positive 10 days later. Human control samples consisted of sera collected from healthy blood donors living in non-Lyme endemic areas (n=5).

Statistical Analysis.

Spearman rank correlation analyses were performed using GraphPad Prism, version 5.0.

Figure 2:
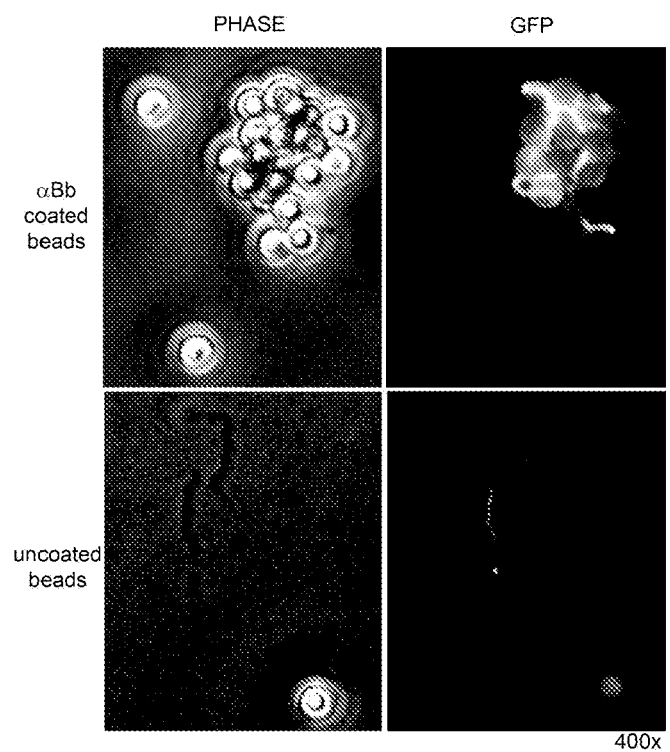
FIG. 2. *B. burgdorferi* captured on magnetic beads provides a reagent for host antibody detection by iPCR. Phase contrast and fluorescent microscopy at 510 nm (GFP) and 400× magnification (400×) was used to determine capture of formalin fixed *B. burgdorferi* expressing green fluorescent protein on beads coated with anti-*B. burgdorferi* polyclonal antibodies (top panels) or uncoated beads (bottom panels).
Figure 3:
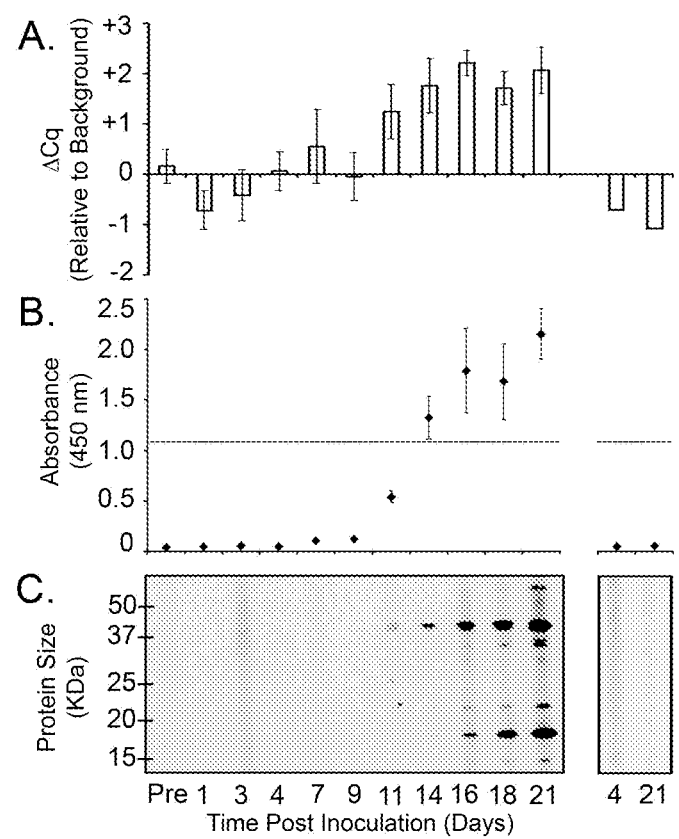
FIG. 3. iPCR demonstrated earlier detection of host response antibodies in *B. burgdorferi* infected mice compared to C6 ELISA and immunoblot. Mouse sera were collected prior to inoculation (pre), at specific days post-intradermal inoculation with $1 \times 10^5$ *B. burgdorferi* B31 A3 (left panels), or from uninfected mice (right panels) over the course of 21 days. (A) Undiluted sera were analyzed for detection of *B. burgdorferi* IgG antibodies using iPCR. Closed system, real time PCR of the DNA reporter molecule was performed using a Taqman-based fluorescent probe assay. The mean quantification cycle (Cq) background signal, determined using uninfected sera plus three standard deviations was designated as the call threshold for a positive detection event and indicated here as $\Delta Cq=0$. Data are shown as the Cq value for each sample minus the mean background Cq plus three standard deviations ($\Delta Cq$). Each data point represents the average of three mice and the standard deviation between samples is shown. (B) C6 ELISA (Immunetics, Inc., Boston, Mass.) was performed according to the manufacturer's instructions with the exception that the secondary antibody was peroxidase-conjugated goat anti-mouse IgM/IgG (1:5000). The threshold absorbance for the test is indicated (horizontal broken line). Each point represents the average of three mice and the standard deviation between samples is shown. (C) Total *B. burgdorferi* sonicate was separated by SDS-PAGE and analyzed by IgM/IgG immunoblot using immune and pre-immune mouse sera diluted 1:200. The positions of the protein standards depict molecular weights in kilodaltons (kDa). Data are representative of three mice analyzed.

Example 1: iPCR Using Intact Spirochetes Provided Earlier Detection of Host Response Compared to Immunoblot and C6 ELISA in a Murine Model The general approach for detection of a host antibody immune response by immunoassay is to use sonicated or otherwise disrupted organisms to generate protein antigens for antibody capture and subsequent detection. However, it was hypothesized that this approach may have limited success for effectively capturing anti-B. burgdorferi antibodies in experimentally infected mouse sera as the majority of the B. burgdorferi proteins in the total cell lysate are not likely to be immunogenic. Although B. burgdorferi lysate is known to harbor antigenic proteins recognized by mouse and human immune sera, these proteins represent a small percentage of the total proteins in the lysate and therefore may not provide improved sensitivity of detection of an immune response to B. burgdorferi infection. In an effort to develop a sensitive, objective method for detection of host antibodies against B. burgdorferi antigens, magnetic beads were coated with a polyclonal anti-B. burgdorferi antibody in order to capture formalin fixed intact spirochetes, resulting in the generation of magnetic beads coated with intact spirochetes (FIG. 2). It was believed that this strategy would result in magnetic beads coated in an enriched pool of spirochete antigenic outer surface proteins capable of interacting specifically with host antibodies produced in response to a B. burgdorferi infection. The sensitivity of iPCR using intact spirochetes to capture host antibodies was compared to pre-existing diagnostic methods including a commercial C6 ELISA and immunoblot using an in vivo murine model. iPCR resulted in the earliest objective detection of a positive infection on day 11 post-inoculation (FIG. 3A). In comparison, C6 ELISA and immunoblot exhibited positive detection of anti-B. burgdorferi antibodies at day 14 and day 21 post-inoculation, respectively (FIGS. 3B and 3C). The approximate molecular weights of the immunodominant proteins detected on the immunoblot included 18 kilodaltons (kDa), 23 kDa, 33 kDa, 39 kDa and 66 kDa, which are consistent with the sizes of the bands typically present on a Lyme disease diagnostic immunoblot. Uninfected mouse serum was negative by all three methods at all time points tested (FIG. 3).

Figure 4:
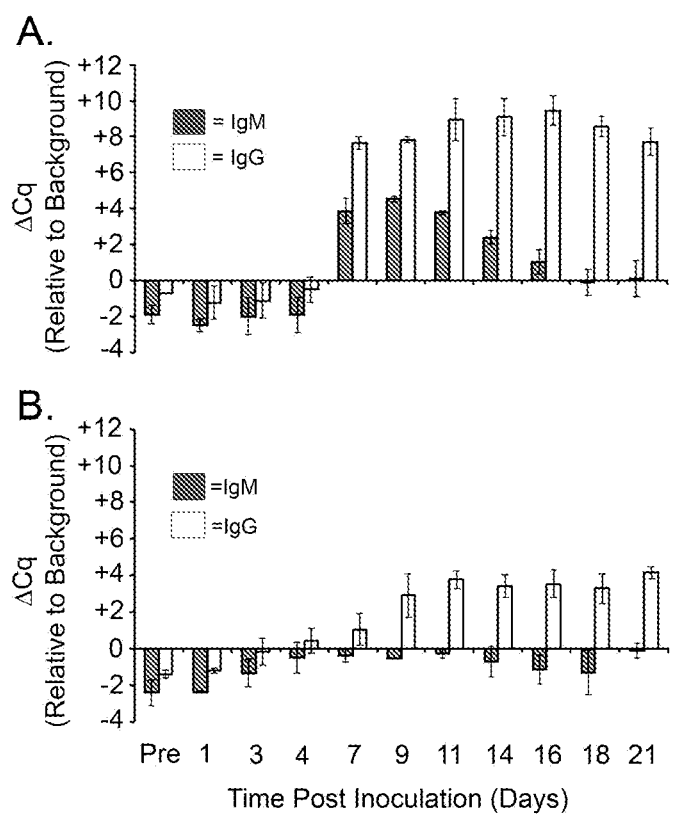
FIG. 4. iPCR using recombinant antigens OspC and BmpA provided enhanced detection sensitivity for both IgG and IgM isotypes in a murine model of infection. Magnetic beads coated with either purified recombinant GST-OspC (A) or GST-BmpA (B) protein were used to capture host response antibodies from pre-immune (pre) or post-immune mouse sera collected over a time period of 21 days. IgM- and IgG-specific reporter antibody-DNA conjugates detected anti-*B. burgdorferi* antibodies captured by each set of antigen coated beads. The IgM (gray bars) and IgG (white bars) response to each antigen was determined for each mouse by multiplex quantitative PCR using distinct probes specific for the IgM- and IgG-specific DNA reporters molecules. The mean quantification cycle (Cq) background signal, determined using uninfected sera plus three standard deviations was designated as the call threshold for a positive detection event and indicated here as $\Delta Cq=0$. Data are shown as the Cq value for each sample minus the mean background Cq plus three standard deviations ($\Delta Cq$). Each data point represents the average of two mice and the standard deviation between samples is shown.

Example 2: iPCR Using Recombinant GST-OspC and GST-BmpA Provided Improved Sensitivity of Detection of Murine Host Antibodies Although beads coated with intact in vitro grown spirochetes provided early detection of anti-B. burgdorferi antibodies as compared to the C6 ELISA and immunoblot (FIG. 3), it was hypothesized that specific recombinant antigens known to be actively expressed during murine infection could potentially result in a more sensitive approach. Known B. burgdorferi in vivo-expressed antigens OspC and BmpA (2) were produced and purified as recombinant N-terminal GST-tagged fusion proteins in E. coli. Magnetic beads coated with either recombinant protein were used to capture host antibodies generated against OspC or BmpA, respectively, and IgM and IgG antibodies against each protein were individually quantitated using an iPCR assay. GST-OspC coated beads resulted in a marked increase in detection of host antibodies starting at day 7 post inoculation for both IgG and IgM (FIG. 4A) with a gradual decrease in IgM back to baseline by day 21 and a minimal decrease in IgG signal to the same time point. GST-OspC-coated beads provided a dramatic increase in the level of IgG detection ($\Delta Cq=10$) as compared to the level of iPCR detection of host antibodies using intact spirochete-coated beads ($\Delta Cq=2.5$). GST-BmpA-coated beads provided robust positive detection of IgG antibodies beginning at day 9 followed by a minimal decrease in the detection signal out to day 21 (FIG. 4B). IgM antibodies directed against BmpA demonstrated a slight increase in signal over the 21 day time course of infection but were not significantly detected above background, suggesting that BmpA does not elicit a serodiagnostic IgM response. Together these data suggest that the use of magnetic beads coated with specific recombinant B. burgdorferi in vivo-expressed antigens results in robust iPCR detection of a humoral response in mice experimentally infected with B. burgdorferi and development of an iPCR assay that quantitates the host response to multiple B. burgdorferi antigens may result in an improved diagnostic method.

Figure 5:
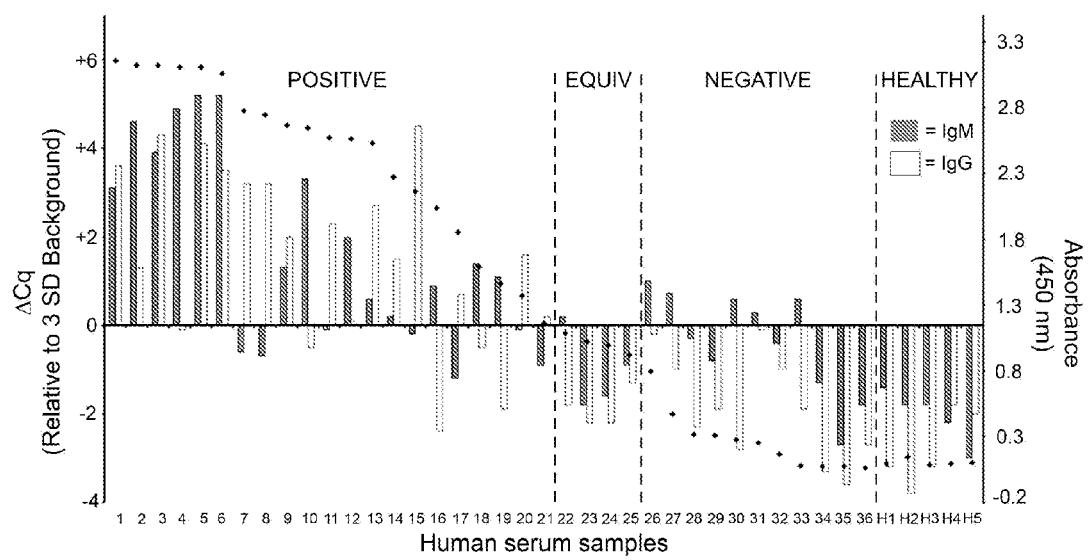
FIG. 5. Recombinant antigen iPCR successfully quantified *B. burgdorferi* VlsE C6 peptide antibodies in human serum samples. Results for 36 serum samples from 18 Lyme disease patients collected upon initial visit to a clinic and at a 10 day follow up visit and 5 healthy controls using a multiplex iPCR protocol to quantitate both IgM (gray bars) and IgG (white bars) isotypes using recombinant *B. burgdorferi* VlsE C6 peptide coated magnetic beads. A call threshold ($\Delta Cq=0$) was assigned at greater than or equal to three standard deviations above the mean background signal determined using serum from healthy individuals. Serum samples were also tested using a commercial C6 ELISA (Immunetics, Boston, Mass.) (diamonds), which was performed according to manufacturer protocol with a call threshold for an absorbance (450 nm) of 1.1 used according to the manufacturer's protocol. The C6 ELISA value represents combined measurement of C6 IgM and IgG antibodies. The patient data (1-36) are grouped into three categories.

Example 3: iPCR Demonstrated a Strong Correlation with a Commercial ELISA for Detection of Host Antibodies in Human Serum Using the VlsE C6 Peptide As recommended by the CDC, the first step of two-tier testing for Lyme disease is the use of a sensitive enzyme immunoassay. Although a number of commercial kits exist for testing, the C6 peptide of the VlsE locus has been shown to be a sensitive and effective predictor for follow-up testing by immunoblot and is available as a commercial testing kit. In order to directly compare the ability of an iPCR assay to detect human antibodies produced against the VlsE C6 peptide with that of an FDA-approved C6 antibody detection method, a panel of human serum samples that consisted of samples from 18 individuals collected at both an initial visit to the clinic and a ten day follow up appointment (n=36) along with sera collected from 5 healthy patients from non-Lyme endemic areas were analyzed by iPCR and using the C6 Lyme ELISA (Immunetics, Inc., Boston, Mass.). iPCR detection of C6-specific host antibodies demonstrated a strong correlation with that of the commercial C6 ELISA ($r_s$=0.895, P<0.0001) (FIG. 5). The iPCR assay differed from the C6 ELISA in that the iPCR assay provided a separate measurement of C6 IgM and C6 IgG antibodies as opposed to the C6 ELISA which quantitated a combined value for both C6 IgM and C6 IgG antibodies. Therefore, the iPCR result was considered positive if C6 IgM and/or C6 IgG antibodies were detected at or above the established call threshold. All 21 samples that demonstrated a positive result by the C6 ELISA were also positive according to C6 iPCR (FIG. 5). Of the four samples determined to be equivocal by the C6 ELISA, three of the sera were found to be negative by C6 iPCR; whereas, one sample tested positive for IgM using this method. Furthermore, of the 11 serum samples that tested negative by C6 ELISA, five of those sera resulted in positive detection of IgM by C6 iPCR. Of note, all iPCR positive samples in this group had ΔCq values of 1 or below. All serum samples collected from known healthy individuals tested negative by both C6 ELISA and C6 iPCR. Together these results suggested that iPCR may have improved ability to detect host antibodies to the VlsE C6 peptide compared to a current commercial method.

Example 4: iPCR Directly Detected *B. burgdorferi* in Blood

The demonstrated power of iPCR to detect ultra-low protein levels (9) suggests that this method may be a promising tool for direct detection of *B. burgdorferi* in clinical samples. iPCR was shown to be successful for capture of live *B. burgdorferi* using magnetic beads coated with polyclonal anti-*B. burgdorferi* antibodies (FIG. 2). This finding suggested the potential for iPCR to directly quantitate spirochetes from within patient samples. To test the sensitivity of iPCR detection of spirochetes, in vitro grown *B. burgdorferi* were serially diluted in HN buffer ($10^6$-$10^2$ spirochetes). iPCR detection of spirochetes demonstrated a robust dilution curve and a level of detection of less than 1,000 organisms (FIG. 6A). Detection of in vitro grown *B. burgdorferi* spiked into whole uninfected mouse blood resulted in a ten-fold lower limit of detection of 10,000 spirochetes (data not shown), suggesting that components of the blood may have an inhibitory effect on the function of the iPCR assay. To correlate the sensitivity of iPCR detection of spirochetes in blood with quantitation of the number of spirochetes present in the blood of infected mice, cohorts of mice were infected with $1\times10^5$ *B. burgdorferi* B31 A3 and blood samples collected every 24 hours for a period of fourteen days. The number of spirochetes/ml of blood, as determined by cfu counts on solid medium, were found to increase over the first week of infection and reached a peak number of approximately 2,500 spirochetes/ml of blood on day 8 post-inoculation (FIG. 6B). The *B. burgdorferi* colonies that grew out of the infected blood within the solid BSK medium demonstrated morphology and growth pattern similar to what is typically observed for spirochete colonies derived from in vitro grown cultures (data not shown). Together, these data suggest that although iPCR is a promising method for direct detection of spirochetes in *B. burgdorferi* infected samples, the sensitivity of the method is currently below the required level of detection.

Discussion Related to Examples 1-4

There is a critical need for development of innovative methods for improved diagnosis of Lyme disease. Disclosed herein is the first application of iPCR for detection of host antibodies against *B. burgdorferi* in both a murine model and human sera.

iPCR Using Recombinant *B. burgdorferi* In Vivo-Expressed Antigens is a Sensitive Method for Detection of Host Response Antibodies in Infected Mice.

An iPCR assay that incorporated attachment of intact spirochetes to magnetic beads provided approximately equivalent sensitivity to current diagnostic methods including C6 ELISA and immunoblot when tested in a murine model. However, it is well known that *B. burgdorferi* can alter its surface protein expression based on its environment. These data have led to the conclusion that in vitro grown spirochetes likely do not present equivalent amounts and types of surface proteins as would be encountered by the host immune system in an active *B. burgdorferi* infection and suggest that the use of multiple in vivo-expressed recombinant antigens may improve assay sensitivity (Stanek G, Strle F. 2009. Lyme borreliosis: a European perspective on diagnosis and clinical management. Curr Opin Infect Dis 22:450-454).

It was hypothesized that saturating the magnetic beads with recombinant in vivo-expressed antigenic proteins would provide more binding targets and hence higher sensitivity than intact spirochetes. This was evident in the fact that active infection was detected on day 7-9 post-inoculation using recombinant antigen coated beads as compared to day 11 using intact spirochete coated beads and with a stronger signal above background, ΔCq=5-10 compared to ΔCq=2.5, respectively. This approach also provides the opportunity to utilize multiple specific antigens either in a combined or individual assay that can be objectively quantified by qPCR.

Recombinant Antigen iPCR Successfully Quantified *B. burgdorferi* VlsE C6 Peptide Antibodies in Human Serum Samples.

An iPCR assay employing a recombinant C6 peptide was developed and compared to an existing commercial kit that uses the same antigen. iPCR detection of C6 antibodies in human sera demonstrated a strong correlation with that of the commercial C6 Lyme ELISA. The C6 ELISA assay results in a combined score for detection of both IgG and IgM isotypes. To provide an additional level of discrimination, the iPCR protocol separately quantitates IgG and IgM antibodies using distinct qPCR template tags and fluorophores, resulting in an individual IgG and IgM iPCR score for each serum sample. All C6 ELISA positive sera were found to be positive for IgG and/or IgM C6 antibodies by iPCR. The added ability of the iPCR assay to differentially quantitate antibody isotypes for a specific antigen of interest in a single sample may provide important information regarding the disease stage at the time of testing.

Of the serum samples that were found to be equivocal or negative by C6 ELISA, a subset of samples in each category was found to be positive by the C6 iPCR assay. These results imply that the iPCR assay may have increased sensitivity of detection over the C6 ELISA; however, further analysis of a larger serum panel is required to fully support this finding. Serum samples from "healthy" individuals with no known exposure to *B. burgdorferi* tested negative by both C6 ELISA and iPCR, suggesting equivalent specificity for the two methods. However, considering the small sample size (n=5), additional samples need to be tested to confirm this result.

iPCR has the Potential for Direct Detection of Spirochetes in Infected Samples.

In an effort to test applicability of iPCR for direct detection of spirochetes within a sample, it was determined that 1,000 spirochetes were needed in buffer and 10,000 organisms where needed in blood. In the murine model used for development of the protocol, the maximum spirochete load in blood was measured to be approximately 2,500 spirochetes/ml. Therefore, the current protocol is unable to directly detect spirochetes during an active murine infection. It has been estimated that the average number of cultivable *B. burgdorferi* cells per ml of whole blood in humans is approximately 0.1 spirochetes per ml and therefore re-isolation of spirochetes from blood has demonstrated limited efficacy when using small volumes of blood (Wormser G P, Bittker S, Cooper D, Nowakowski J, Nadelman R B, Pavia C. 2001. Yield of large-volume blood cultures in patients with early Lyme disease. *J Infect Dis* 184:1070-1072). Hence, an alternative approach has been proposed to sample blood cultures and test by qPCR for increasing amounts of spirochete DNA (Schwartz I, Bittker S, Bowen S L, Cooper D, Pavia C, Wormser G P. 1993. Polymerase chain reaction amplification of culture supernatants for rapid detection of *Borrelia burgdorferi*. Eur J Clin Microbiol Infect Dis 12:879-882). While an enrichment step is practical, the use of qPCR has the potential to introduce false positive results from contaminating *B. burgdorferi* template DNA in the laboratory and typically requires additional protocol steps for nucleic acid purification. iPCR, which herein has demonstrated successful detection of spirochetes directly from whole blood and is much less prone to the same contamination issues as the PCR template is unrelated to *B. burgdorferi* and human DNA, could effectively be used to make a more rapid diagnosis from *B. burgdorferi* infected blood cultures. Furthermore, as *B. burgdorferi* is transiently present in the blood of infected patients the iPCR method may also be adapted for direct detection of spirochetes in synovial fluid and/or cerebral spinal fluid. Direct detection of spirochetes in patient samples is not anticipated to serve as the sole method for diagnosis of Lyme disease, rather in conjunction with sensitive and specific detection of *B. burgdorferi* antibodies.

Contributions of an iPCR-Based Approach Using Recombinant Antigens to Future Automated Lyme Disease Diagnostics.

The field of Lyme disease diagnostics is challenged by two main issues, a lack of consistent reagents and the need for a more simplified objective form of testing. There are currently multiple commercial assays that use a range of antigen types from single recombinant antigens to multiple antigens to whole sonicated organisms. One principal focus for the field has been on the use of purified, recombinant, or synthetic peptides as the source of antigens in immunoassays. Unfortunately, no single antigen has demonstrated sufficient sensitivity and specificity to warrant replacing two-tier testing. Protein expression differences among species and temporal appearance of relevant antibodies to different antigens at various stages of Lyme disease make the choice of a single antigen a difficult task and makes the combined use of antigens an attractive alternative. The results presented here suggest that iPCR combined with the use of recombinant *B. burgdorferi* in vivo-expressed antigens has the potential to provide improved sensitivity of detection in an objective format that can be used to detect multiple host response antibodies and isotypes. Moreover, future translation of this method to an automated point-of-care platform will allow for objective routine testing of Lyme disease patients.

Example 5: Identification of Capture Antigens for Robust Detection of *B. burgdorferi* Antibodies from Mouse Immune Sera The efficacy of the iPCR assay is expected to be dramatically enhanced by coating the capture beads with only those in vivo expressed *B. burgdorferi* antigens with strong reactivity to immune serum. In one embodiment, the recombinant hybrid peptide VOVO is used, which is composed of multiple immunodominant peptide sequences (VIsE and OspC) from divergent species of LD spirochetes and has demonstrated strong antigenicity across a diverse panel of human LD patient sera (Burbelo, P. D., et al., Rapid, simple, quantitative, and highly sensitive antibody detection for lyme disease. Clin Vaccine Immunol, 2010. 17(6): p. 904-9). In addition, a novel recombinant hybrid peptide VOVOK157 is generated, which along with the VOVO sequence includes single copies of immunodominant peptides 1, 5 and 7 from BBK07, which have been suggested to have the potential to enhance the diagnostic power of VIsE and OspC based immunoassays (Coleman, A. S., et al., BBK07 immunodominant peptides as serodiagnostic markers of Lyme disease. Clin Vaccine Immunol, 2011. 18(3): p. 406-13.). Further, a panel of individual purified recombinant in vivo-expressed *B. burgdorferi* antigens is generated, which are herein realized as candidates for immunodiagnosis of Lyme disease including serodiagnostic OspC types A, B, E, F and K, the VIsE C6 peptide, BmpA (P39), BBK32, CRASP-2, DbpA, DbpB, FliL, BBK19, BBK07, BBP34, BB0329, BB0680, Lmp1N, RevA, BB0765 (Aguero-Rosenfeld, M. E., et al., Diagnosis of lyme borreliosis. Clin Microbiol Rev, 2005. 18(3): p. 484-509. Barbour, A. G., et al., A genome-wide proteome array reveals a limited set of immunogens in natural infections of humans and white-footed mice with *Borrelia burgdorferi*. Infect Immun, 2008. 76(8): p. 3374-89. Brissette, C. A., et al., The borrelial fibronectin-binding protein RevA is an early antigen of human Lyme disease. Clin Vaccine Immunol, 2010. 17(2): p. 274-80. Crother, T. R., et al., Temporal analysis of the antigenic composition of *Borrelia burgdorferi* during infection in rabbit skin. Infect Immun, 2004. 72(9): p. 5063-72. Feng, S., et al., Humoral immunity to *Borrelia burgdorferi* N40 decorin binding proteins during infection of laboratory mice. Infect Immun, 1998. 66(6): p. 2827-35. Heikkila, T., et al., Species-specific serodiagnosis of Lyme arthritis and neuroborreliosis due to *Borrelia burgdorferi* sensu stricto, *B. afzelii*, and *B. garinii* by using decorin binding protein A. J Clin Microbiol, 2002. 40(2): p. 453-60. Liang, F. T., et al., An immunodominant conserved region within the variable domain of VIsE, the variable surface antigen of *Borrelia burgdorferi*. J Immunol, 1999. 163(10): p. 5566-73. Nowalk, A. J., R. D. Gilmore, Jr., and J. A. Carroll, Serologic proteome analysis of *Borrelia burgdorferi* membrane-associated proteins. Infect Immun, 2006. 74(7): p. 3864-73. Poljak, A., et al., Identification and characterization of *Borrelia* antigens as potential vaccine candidates against Lyme borreliosis. Vaccine, 2011. Roessler, D., U. Hauser, and B. Wilske, Heterogeneity of BmpA (P39) among European isolates of *Borrelia burgdorferi* sensu lato and influence of interspecies variability on serodiagnosis. J Clin Microbiol, 1997. 35(11): p. 2752-8. Wilske, B., et al., Immunological and molecular polymorphisms of OspC, an immunodominant major outer surface protein of *Borrelia burgdorferi*. Infect Immun, 1993. 61(5): p. 2182-91. Zuckert, W. R., J. Meyer, and A. G. Barbour, Comparative analysis and immunological characterization of the *Borrelia* Bdr protein family. Infect Immun, 1999. 67(7): p. 3257-66.).

All recombinant proteins are typically engineered without their respective signal peptide, if applicable, and produced as translational fusions to glutathione-S-transferase (GST) at the N-terminus in *E. coli* using expression vector pGEX-6P-1. Recombinant *B. burgdorferi* antigen labeled magnetic beads are used to capture *B. burgdorferi* antibodies from pre-immune and immune mouse sera, collected at days 3, 7, 11 and 21 post inoculation with WT *B. burgdorferi*. Two reporter antibody-DNA conjugates will be generated to specifically detect anti-*B. burgdorferi* IgM versus IgG antibodies. Multiplex quantitative PCR combining the IgM- and IgG-specific DNA reporter molecules will be used to determine the mouse humoral response to each antigen at the different time points of infection. The efficacy of each antigen-specific assay will be determined by the ΔCq value for each reporter at each time point. Those antigens that demonstrate robust detection of anti-*B. burgdorferi* IgM and/or anti-*B. burgdorferi* IgG (ΔCq≥0) are selected for further analysis in Aim 1c. Antigens that demonstrate IgM detection at day 21 in the absence of IgG are regarded as non-specific and removed from the panel.

Example 6: Identification of Highly Informative Antigens for Detection of *B. burgdorferi* Antibodies in Human Samples The capture/reporter system for the disclosed *B. burgdorferi* antibody detection assay was designed to use *Borrelia* sp. antigens expressed during mammalian infection. Adaptation of this system for use with human sera only requires that anti-human IgM and IgG antibodies be used as the reporter antibodies, which will be conjugated to the DNA reporter molecules. The panel of antigens that pass the selection criteria outlined in Example 5 above are evaluated by the iPCR assay for detection of anti-*B. burgdorferi* IgM and IgG antibodies in a small cohort training set (n=30) of well characterized, de-identified, retrospective serum samples collected from 10 patients with early stage LD, 10 patients with late stage LD and 10 healthy controls. These sera, along with all others were collected in serum separator tubes, allowed to clot at room temperature, centrifuged, aliquoted into cryo tubes and immediately frozen and preserved at −80° C. The sensitivity, specificity and positive and negative predictive values of each antigen is calculated at various cutoffs using two-by-two contingency tables. The corresponding 95% confidence intervals is constructed using the modified Wald method (Agresti, A. and B. A. Coull, Approximate is better than "exact" for interval estimation of binomial proportions. American Statistician, 1998. 52(2): p. 119-126).

Furthermore, in order to mitigate limitations such as false positives and cross-reactivity any antigen that is positive for IgM antibodies in samples from patients with late stage Lyme disease and/or suggests a specificity of <99% are removed from the panel. To address the clinical need for improved early diagnosis of Lyme disease, antigens that demonstrate robust iPCR IgM and/or IgG values for samples from patients with early stage Lyme diseaseD, as defined by statistically significant ($P<0.05$) higher iPCR values for the early Lyme disease sera compared to the healthy control sera using the Mann-Whitney U test. Using these analyses, a subset of approximately 4-6 hybrid and/or individual recombinant *B. burgdorferi* antigens are detected that indicate high diagnostic power for detection of anti-*B. burgdorferi* antibodies and that in combination are predicted to result in sensitive and specific detection of a humoral response to *B. burgdorferi* infection across all stages of disease. These antigens are combined in equal amounts to generate multi-antigen coated magnetic capture beads for an optimized iPCR assay. Alternatively, novel hybrid antigens are constructed using the panel of top performing antigens. These two approaches overcome the ELISA-based challenge of detection of low immune responses in some samples. The combined use of multiple immunodominant epitopes and the signal amplification power of PCR in the disclosed assay is designed to enhance detection of low affinity and/or low titer antibodies by increasing antibody affinity due to cooperative binding, exposure of more conformational epitopes and exponential increase of the output signal. The diagnostic performance of the optimized iPCR assay is preliminarily evaluated using the above described small cohort training set of serum samples.

Example 7: Identification of Antibodies for Robust Detection of *B. Burgdorferi* In Vivo-Expressed Antigens in the Presence of Biological Matrix The purified recombinant *B. burgdorferi* antigens, generated in Example 5 above are used to produce at least two affinity purified polyclonal antibodies per antigen. Because *B. burgdorferi* does not express the target in vivo antigens (i.e., VlsE, OspC or BBK07) during standard in vitro growth conditions [45, 62], *B. burgdorferi* clones are engineered for constitutive expression of each *B. burgdorferi* antigen to use in the analyses. The titer and specificity of each antibody is determined by immunoblot analysis using protein lysates from the corresponding engineered antigen$^+$ *B. burgdorferi* clone. Those antigen-specific polyclonal antibodies that demonstrate robust sensitivity and specificity by immunoblot will be analyzed as capture and reporter antibodies in an iPCR assay. The sensitivity and specificity of detection of in vitro serially diluted antigen$^+$ *B. burgdorferi* is determined using iPCR. Detection of spirochetes in blood, plasma or serum, adds an additional level of complexity due to the possibility of cross reactivity or inhibition of antigen capture as a result of proteins from the biological sample. Serially diluted numbers of antigen$^+$ *B. burgdorferi*)($10^7$-$10^0$ is spiked into a constant volume of uninfected mouse blood in the presence and absence of anticoagulant. The efficacy of iPCR detection of spirochetes in plasma and serum is analyzed. In parallel, the efficiency of recovery of live spirochetes from each sample is evaluated using solid plating for colony forming units. Similar to the experiments described in Example 5, these experiments involve empirical determination of the amount of capture antibody used to coat the magnetic beads and the length of incubation time needed for optimal capture of *B. burgdorferi* antigens as well as optimization of the blocking buffers and purification of the reporter antibody-DNA conjugates to achieve the highest signal to noise ratio. According to a further embodiment, provided is a polyclonal antibody that detects epitopes on multiple antigens. In a specific embodiment, the polyclonal antibody detects one or more, two or more, or three or more antigens from the following: OspC, BmpA, VlsE(C6), DbpA, BBK19, OspA, RevA, Crasp2, or BBK50.

Example 8: Hybrid Recombinant Antigen

According to a specific embodiment, disclosed is an approach using immuno-PCR (iPCR) and employing a single hybrid recombinant antigen that combines three highly antigenic in vivo-expressed B. burgdorferi antigens for objective highly sensitive and specific detection of a host immune response to B. burgdorferi infection. The hybrid recombinant antigen, referred to herein as 'DOC', (see SEQ ID NO. 1, FIG. 8) comprises the full length DbpA protein fused to the PEP10 peptide of OspC and the C6 peptide of VlsE. In frame glutathione-S-transferase (GST) fusion protein for the DOC hybrid protein was generated using two distinct PCR amplification steps. First, the corresponding coding regions for DbpA and C6 were amplified separately from B. burgdorferi genomic DNA with non-template addition of the PEPC10 sequence to each amplicon using primer pairs P17 and P18 (DbpA-PEPC10) and P19 and P20 (C6-PEPC10) engineered with BamHI/SalI restriction sites (Table 1). Both PCR products were diluted 100-fold, combined and synthetically assembled into the DOC construct by overlapping PCR using primer pairs P17 and P20. Final constructs were sequenced verified and recombinant protein generated and purified as described for previous antigens. The combination of the iPCR approach with a single hybrid antigen alleviates a number of the issues posed to Lyme disease diagnostics. This embodiment when used in the disclosed detection method embodiments provides a single streamlined quantitative test that provides equivalent sensitivity and increased specificity compared to existing two-tier testing. See FIG. 7. iPCR combined with the DOC recombinant antigen only required testing of the IgG antibody fraction for a positive diagnosis and appears to have the potential to determine both the stage and type of disease. This embodiment reduces the cost and complexity of current testing and more importantly provides a means of reagent standardization that has proven to be difficult for many of the existing commercial assays. The combination of the iPCR method with a single hybrid recombinant protein provides a novel method for detection of Lyme disease.

Materials and Methods Related to Examples 9-13

Healthy Human Sera.

The current study was approved by the University of Central Florida's institutional review board (UCF IRB) (FWA00000351 and IRB00001138). All procedures and investigators involved in the sample collection process were approved by the UCF IRB with Collaborative Institutional Training Initiative (CITI) training. All donors provided written consent to participate in the study. Sample collection was undertaken at the University of Central Florida campus. UCF is a diverse community of nearly 60,000 students and approximately 8,000 faculty and staff members of various ages and ethnic and racial backgrounds. Individuals were included in the study if they had not been previously diagnosed with and/or treated for Lyme disease, received a Lyme disease vaccination, or lived within the past 10 years in a state with a high incidence of Lyme disease (Connecticut, Delaware, Maine, Maryland, Massachusetts, Minnesota, New Hampshire, New Jersey, New York, Pennsylvania, Vermont, Virginia, and Wisconsin). Approximately 10 ml of blood was sampled, according to the IRB-approved protocol, from 36 individuals into serum separator tubes, inverted five times to mix the clot activator with the blood, and allowed to clot for ≥30 min. Serum fractions were collected by centrifugation at 1,200×g for 10 min. The serum was further clarified by centrifugation at 9,100×g for 5 min to remove any insoluble material and stored at 4° C. for short-term or −80° C. for long-term storage.

Lyme Disease Human Serum Panel.

The CDC research panel I consisted of patient serum samples collected from 32 individuals, including patients with stage 1, 2, or 3 Lyme disease (n=12), look-alike diseases, including fibromyalgia, rheumatoid arthritis, multiple sclerosis, mononucleosis, syphilis, and severe periodontitis (n=12), as well as healthy individuals from areas of endemicity (n=4) and nonendemicity (n=4) for Lyme disease. All Lyme disease patients were diagnosed by a physician, stage 1 and 2 patients were confirmed by culture and/or PCR detection of B. burgdorferi, and stage 3 patients were positive by two-tiered testing. The CDC-recommended two-tiered testing algorithm (6) was performed using FDA-cleared assays for Lyme disease and consisted of a first-tier whole-cell sonicate enzyme immunoassay (VIDAS Lyme IgM and IgG polyvalent assay; bioMérieux, Inc., Durham, N.C.), followed by second-tier IgM and IgG immunoblots (IB) (MarDx Diagnostics, Inc., Carlsbad, Calif.). The blinded CDC research panel II consisted of serum samples collected from 92 individuals, including patients with stage 1, 2, or 3 Lyme disease (n=32), look-alike diseases, including fibromyalgia, rheumatoid arthritis, multiple sclerosis, mononucleosis, syphilis, and severe periodontitis (n=36), as well as healthy individuals from areas of endemicity (n=12) and nonendemicity (n=12) for Lyme disease. The laboratory support of Lyme disease diagnosis was the same as for CDC research panel I. Prior to analysis, all serum samples were clarified by centrifugation at 9,100×g for 5 min to remove any insoluble material and put in the short-term storage at 4° C.

Cloning and Expression of Recombinant Antigens Lacking GST Fusion Tags.

Recombinant glutathione S-transferase (rGST)-BmpA and rGST-OspC were constructed as previously described (10). In-frame glutathione S-transferase (GST) fusion proteins for BBK19, OspA, DbpA, RevA, Crasp-2, and BBK50 were generated by PCR amplification of the corresponding coding regions, without the signal sequences from B. burgdorferi genomic DNA, using primer pairs 1147 and 1148 (BBK19), 1151 and 1152 (OspA), 1145 and 1146 (DbpA), 1143 and 1144 (RevA), 1149 and 1150 (Crasp-2), or 1043 and 1044 (BBK50) engineered with BamHI and SalI or XhoI restriction sites (Table 2) and Phusion polymerase (New England BioLabs, Ipswich, Mass.). Information about the sequences is found at Barbour et al., Infect Immun. 2008 August; 76(8):3374-89, Kraiczy et al, International Journal of Medical Microbiology, 298:268-271, and U.S. Patent Publication no. US 20120142023, sequence information incorporated herein by reference in the entirety. The PCR products were purified (Qiagen, Valencia, Calif.), digested with the appropriate restriction enzymes (New England BioLabs), and cloned into BamHI- and SalI- or XhoI-digested pGEX-6P-1 (GE Healthcare, Piscataway, N.J.) to generate translational fusions with GST at the N terminus. Subsequent clones were selected and the sequence confirmed by sequence analysis. pGEX-6P-1 plasmids carrying the bmpA, ospC, bbk19, ospA, dbpA, revA, crasp-2, and bbk50 genes were transformed into Escherichia coli strain BL21 (Novagen, Billerica, Mass.). Protein expression was induced by the growth of BL21 cells containing the expression construct for each B. burgdorferi antigen in 50 to 100 ml of MagicMedia E. coli expression medium, according to the manufacturer's protocol (Invitrogen, Carlsbad, Calif.)

for 24 h at 37° C. with aeration. Recombinant protein purification was performed according to the procedures outlined in the Bulk GST purification module (GE Healthcare). The purified proteins were dialyzed in Tris-buffered saline (50 mM Tris-HCl, 150 mM NaCl [pH 7.5]) overnight at 4° C. using D-Tube dialyzers (EMD Millipore Chemicals, Philadelphia, Pa.) and two buffer exchanges to remove excess glutathione. The dialyzed proteins were subjected to protease cleavage of the GST tag overnight at 4° C., according to procedures outlined in the PreScission protease kit (GE Healthcare). Cleaved proteins were purified from GST and excess protease using two rounds of Bulk GST purification (GE Healthcare) and collection of the eluent. Purified proteins lacking a GST tag were concentrated using Amicon Ultra-2 centrifugal filter devices (EMD Millipore Chemicals) to a volume of approximately 80 µl and stored at 4° C. The total protein content was quantified by absorbance spectrophotometry at a wavelength of 280 nm. Recombinant protein purity and seroreactivity were determined by Coomassie gel staining and immunoblot using infected mouse serum. Briefly, 100 ng of each recombinant protein was separated by 12.5% polyacrylamide gel electrophoresis. For Coomassie staining, the gels were incubated in Imperial protein stain (Thermo Scientific, Rockford, Ill.) for 1 h and destained in deionized water for 1 h prior to imaging. For immunoblot analysis, the proteins were transferred to a nitrocellulose membrane, and the membrane was blocked in 5% skim milk and incubated for 1 h with mouse serum samples collected 3 weeks postinoculation with wild-type *B. burgdorferi*, as previously described (10), diluted 1:200 in Tris-buffered saline-0.05% Tween (TBST) (pH 7.6), washed twice with TBST, incubated with horseradish peroxidase (HRP)-conjugated goat anti-mouse IgG/IgM (Chemicon International, Billerica, Mass.) for 1 h, washed twice with TBST, and the signal was detected using the SuperSignal West Pico chemiluminescent substrate kit (Thermo Scientific).

Cloning and Expression of the Recombinant DOC Antigen.

An in-frame glutathione S-transferase (GST) fusion protein for the DOC hybrid protein was generated using two distinct PCR amplification steps. First, the corresponding coding regions for DbpA and the C6 peptide of VlsE (11) were amplified separately from *B. burgdorferi* strain B31 genomic DNA, and the PEPC10 sequence (12) was added to each amplicon using the primer pairs 1145 and 1084 (DbpA-PEPC10) and 1085 and 1023 (C6-PEPC10), respectively, engineered with BamHI/SalI restriction sites (Table 2). Both PCR products were diluted 100-fold, combined, and synthetically assembled into the DOC construct by overlapping PCR using the primer pairs 1145 and 1023. The final constructs were sequenced and verified, and the recombinant protein was generated and purified as described above for the other *B. burgdorferi* antigens.

iPCR Reagents, Assay, and Signal Amplification.

iPCR reagents were prepared and the assays conducted as previously described (Halpern et al. Clin Vaccine Immunol 2013 Mar. 9; 20(3):350-7), with minor modifications. Briefly, iPCR assays were assembled in a two-sided (sandwich) manner, as detailed in FIG. 9A, with the capability to simultaneously capture and report both IgM and IgG host-generated antibodies (FIG. 9B). Recombinant antigens lacking fusion tags were used to coat magnetic beads for host antibody capture using 10 to 20 µg of antigen per mg of beads. The beads were resuspended in 500 µl TBST for secondary antibody incubation. Signal amplification by real-time quantitative PCR was accomplished as previously described (Halpern et al. supra), and the quantification cycle (Cq) for each reaction was determined using a manual baseline determination (cycle 10 to 20) and a manual threshold setting of 1.0.

The PCR plate set-ups for all experiments included, in duplicate, a PCR-negative template control consisting of water and an iPCR bead processing negative control that contained the TBST stock used for processing to determine the sample-to-sample contamination. Additionally, each PCR run included calibrator plasmids carrying the cloned template for the IgM or IgG reporter oligonucleotides that were used to account for run-to-run variation in the threshold calculation between the PCR plates. Briefly, the baseline was manually adjusted such that the Cq values for the calibrator plasmids were set at a constant value for each plate to account for minor variability in the threshold setting.

Positive Threshold Value and Data Analysis.

The results of the Lyme disease iPCR assay were reported as ΔCq values. The ΔCq value was calculated as the difference between the antigen-/isotype-specific background threshold Cq value and the Cq value of the sample. The antigen-/isotype-specific background threshold Cq values were calculated as the mean Cq value of each antigen-isotype combination for a group of 16 healthy individuals minus a specific multiple of the standard deviation (SD) of the mean. The antigen-specific multiplier was set at a minimal value (1.9 to 6.6 for IgM and 3.1 to 5 for IgG), such that the samples from all individuals without Lyme disease in CDC research panel I resulted in a Lyme disease iPCR ΔCq value of <0. Using these antigen-/isotype-specific thresholds, any sample that resulted in a Lyme disease iPCR ΔCq of 4 was called iPCR positive. The coefficient of variation (CV) was calculated as the ratio of the SD to the mean. Assay sensitivity and specificity and the associated 95% confidence intervals were calculated using GraphPad Prism 5.0 for Windows (Graph Pad Software).

Example 9: Lyme Disease iPCR Demonstrates Strong within-Assay Precision and Reproducible Background Across a Sample Population of Healthy Individuals It was previously demonstrated proof-of-principle for iPCR detection of human host-generated *B. burgdorferi* antibodies using VlsE C6 peptide-coated magnetic beads and a panel of serum samples (n=36) from Lyme disease-positive and Lyme disease-negative patients and healthy controls (10). This feasibility study was accomplished using a small number of samples from healthy controls (n=5) to determine test efficiency and background threshold levels. In an effort to establish a better understanding of the performance of the Lyme disease iPCR assay, including the repeatability and the variability of the background of the assay across a healthy population, the number of replicates and overall sample size of healthy individuals were expanded. Prospective blood samples were collected from consenting individuals without a history of Lyme disease under the approval of the University of Central Florida's institutional review board. To assess assay repeatability, a serum sample from a single healthy individual was tested 18 times using the same reagent preparation lots, including DbpA antigen-coated beads and oligonucleotide-labeled secondary antibodies. The DbpA protein was selected as a representative in vivo-expressed *B. burgdorferi* antigen. The results of this analysis demonstrated low within-assay variability for both the IgM- and IgG-specific detection reagents, as indicated by standard deviation values for each data set of 0.39 and 0.73, respectively, and coefficient of variation values for each data set of 1.34% and 2.30%, respectively (FIG. 10).

To determine the variability in the background of the Lyme disease iPCR assay across a healthy human population, the serum samples from 36 healthy individuals were tested in duplicate using magnetic beads coated with the DbpA antigen and the oligonucleotide-labeled IgM and IgG secondary antibodies used for the repeatability analysis. Similar to the within-sample repeatability analysis, the results of the between-sample variability analysis demonstrated a standard deviation across the population of 0.79 for the background detection of IgM antibodies and 0.84 for IgG antibodies; the coefficients of variation were 2.66% and 2.63%, respectively (FIG. 11).

Example 10: Mean and Standard Deviation Background Values Across a Population of Healthy Individuals are Unique for Each Lyme Disease iPCR Assay Antigen-Isotype Combination The analysis of the Lyme disease iPCR assay repeatability and population variability using DbpA-coupled magnetic beads demonstrated that the mean background value for the detection of IgM versus IgG antibodies differed by as much as ~2.5 Cq values (FIGS. 10 and 11). Based on this observation, it was predicted that depending on the different antigen used, each Lyme disease iPCR assay would result in a distinct mean background Cq value. If true, this finding would impact the determination of the background threshold setting for the assay, making it necessary to assign a distinct background threshold for each antigen-isotype combination. To test this hypothesis, a list was compiled from the literature of B. burgdorferi proteins that are known or hypothesized to be seroreactive in humans (13-27). From this list, a subset of 8 B. burgdorferi antigens was selected for further analysis in the assay due to their ability to be produced in large quantities as recombinant in-frame N-terminal glutathione S-transferase (GST) fusion proteins in E. coli. To eliminate any possibility of antibody cross-reactivity to the GST tag, this sequence was proteolytically removed. The purity and antigenicity of each recombinant antigen were demonstrated by SDS-PAGE, followed by Coomassie brilliant blue staining and immunoblot analysis using pooled sera collected from B. burgdorferi-infected mice (see FIG. 16).

Each antigen was coupled to magnetic beads and examined by Lyme disease iPCR for both IgM and IgG background reactivities across 16 serum samples collected from healthy individuals. As predicted, all antigen-isotype combinations demonstrated unique background values that ranged from a mean Cq of 26.09 to 32.46 for IgM and 25.30 to 36.62 for IgG and a standard deviation of 0.40 to 1.53 for IgM and 0.37 to 1.47 for IgG (FIG. 12).

Example 11: Multiplex iPCR Detection of IgM and/or IgG Host Response Antibodies Against B. burgdorferi Using a Panel of Antigens has the Potential for Improved Sensitivity Compared to 2-Tier Testing Most existing protocols for Lyme disease diagnostics require the use of multiple antigens to diagnose the disease. In an effort to further explore the application of iPCR as a Lyme disease diagnostic, a methodology that utilizes a combination of results for different antigens to facilitate diagnosis was pursued. The panel of eight B. burgdorferi antigens was tested against the CDC research panel I collection of sera using multiplex iPCR for the simultaneous detection of IgM and IgG host-generated antibodies. The same human serum panel was previously tested according to CDC guidelines by a commercial enzyme-linked immunosorbent assay (ELISA), followed by IgM and IgG immunoblot (IB), and classified for 2-tier testing status (see Table S1). Samples were considered positive by iPCR if they resulted in a $\Delta Cq$ value that was $\geq 0$ for IgM or IgG for one or more of the eight antigens tested. The $\Delta Cq$ value was calculated as the difference between the antigen-/isotype-specific background threshold Cq value and the Cq value of the sample. The antigen-/isotype-specific background threshold Cq values were calculated as the mean Cq value of each antigen-isotype combination for a group of 16 healthy individuals minus a specific multiple of the standard deviation (SD) of the mean (FIG. 12). Each antigen-specific multiplier was set at a minimum value (1.3 to 6.6 for IgM and 2.8 to 5 for IgG; see Table S2), such that the samples from all individuals without Lyme disease in CDC research panel I resulted in a Lyme disease iPCR $\Delta Cq$ value of <0. Using these criteria, iPCR testing provided similar results to those of 2-tier testing for the Lyme disease patient samples, with one exception (see Table S1). A single early Lyme disease patient sample that was deemed negative by 2-tier testing was positive by iPCR (see Table S1, sample A4). It should also be noted that no single antigen provided iPCR-positive results across all Lyme disease patient samples, which comprised different stages and clinical presentations of disease.

Figure 14A:
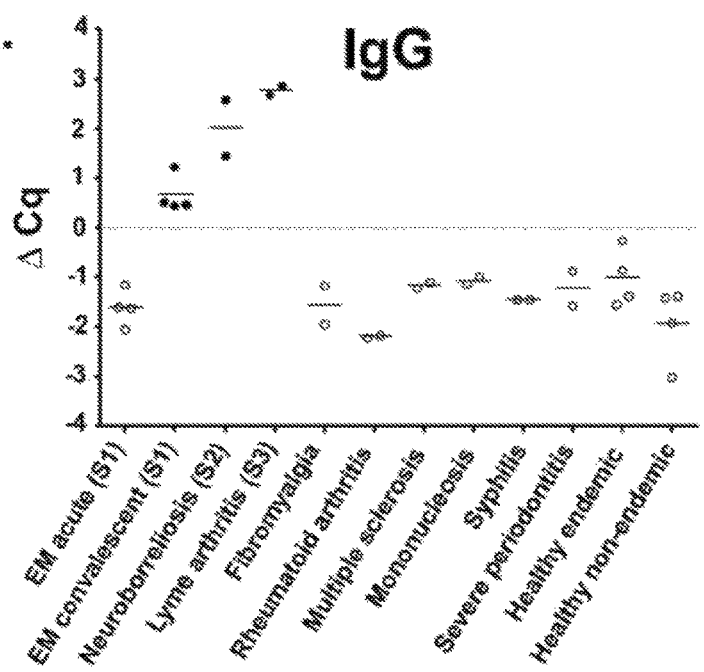
Figure 14B:
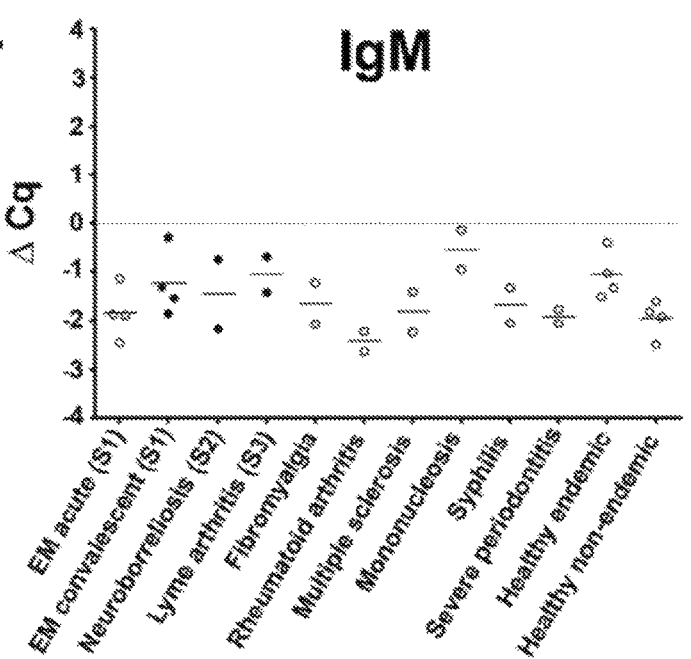

Example 12: Simplified Single Hybrid Antigen iPCR Detection of Host-Generated IgG Antibodies Alone Confirms 2-Tier Results for a Panel of Human Serum Samples iPCR testing with the panel of eight B. burgdorferi antigens showed strong potential as a Lyme disease diagnostic method by reproducing the 2-tier test results for CDC research panel I Lyme disease patient samples. Although successful, the use of multiple antigens tested against IgM and IgG increases test complexity by requiring the testing of a single sample with multiple antigens. In an effort to further simplify the Lyme disease iPCR approach, it was theorized that a single hybrid antigen composed of the immunogenic epitopes of multiple B. burgdorferi antigens would provide results similar to those of testing with a panel of whole individual antigens. To examine the applicability of a single hybrid antigen for iPCR detection of host-generated antibodies against B. burgdorferi infection, a novel hybrid antigen composed of full-length DbpA, the PEPC10 peptide (OspC), and the C6 peptide (VlsE), referred to as the DOC antigen (FIG. 13A) was synthetically constructed. Similar to the previous eight recombinant antigens, it was determined that the protein purity and seroreactivity toward B. burgdorferi-infected mouse sera of the hybrid protein (see FIG. 16). The range of the background reactivity of the DOC antigen in the iPCR assay was determined using the serum from a group of 16 healthy individuals (FIG. 13B). The results of the between-sample variability analysis demonstrated a standard deviation across the population of 0.57 for the background detection of IgM antibodies and 0.51 for the background detection of IgG antibodies; the coefficients of variation were 2.31% and 1.94%, respectively. Using iPCR, then tested was the hybrid antigen in duplicate against the CDC research panel I for IgM and IgG reactivity, utilizing the results to establish the positive call threshold as described above. The DOC antigen IgG results confirmed all 2-tier-positive results (FIG. 14A). Interestingly, the Lyme disease iPCR assay using the DOC antigen tested negative for the detection of host-generated IgM antibodies for all human samples analyzed (FIG. 14B).

Although early, specific diagnosis is the primary goal for any Lyme disease diagnostic, determining the stage of disease progression would provide additional information to aide in the treatment of the disease. It is logical to assume that the amount of host-generated B. burgdorferi antibody will increase with further disease progression. Due to the quantifiable nature of iPCR testing, it was hypothesized that the amount of anti-DOC host-generated IgG antibody correlates with disease stage. The mean±SD iPCR value was −1.61±0.36 for stage 1 acute early Lyme disease patients, 0.67±0.38 for stage 1 convalescent early Lyme disease patients, and 2.39±0.64 for stage 2/stage 3 Lyme disease patients, for a total of n=4 samples per group. These data may suggest a correlation of increasing antibody capture with disease progression; however, further evaluation with an increased number of clinically defined samples is required to support this finding. It should also be noted that the number of EM rashes documented for each patient showed no correlation with the iPCR value for B. burgdorferi antibody detection (data not shown).

Example 13: DOC Hybrid Antigen iPCR Demonstrates Robust Sensitivity and Specificity for a Blinded Panel of Human Serum Samples The initial success of DOC IgG iPCR with replicating 2-tier results for a panel of 32 human serum samples provided strong evidence for the application of the disclosed approach as a simplified Lyme disease diagnostic. Next sought was to perform a larger-scale blinded validation analysis of an assay. The CDC research panel II, composed of 92 samples, including sera collected from patients with early Lyme disease and EM (stage 1), early Lyme disease with neurological or cardiac evidence of dissemination (stage 2), and patients with Lyme arthritis (stage 3), as well as look-alike diseases and healthy donors, was tested by iPCR for host-generated IgG antibodies to the DOC hybrid antigen, and the results were compared to those of the 2-tier test (Table 3). Using the background threshold Cq value for DOC/IgG established above, overall, iPCR provided levels of sensitivity and specificity comparable to those of 2-tier testing (FIG. 15). iPCR replicated all 2-tier-positive results. Moreover, iPCR provided detection of an additional three early Lyme disease samples deemed negative by 2-tier testing, leading to an overall sensitivity for iPCR of 69% (95% confidence interval [CI], 50% to 84%) compared to the sensitivity of 2-tier testing of 59% (95% CI, 41% to 76%). The difference in sensitivity was entirely for detecting stage 1 early Lyme disease samples, with sensitivity for iPCR of 55% (95% CI, 32% to 77%) and of 40% for 2-tier testing (95% CI, 19% to 64%) for this category of samples. iPCR and 2-tier testing showed equivalent sensitivity for stage 2/stage 3 Lyme disease samples of 92% (95% CI, 62% to 100%). iPCR detected only a single false positive for a sample from a healthy control from an area of endemicity (healthy endemic sample), resulting in a specificity of 98% (95% CI, 91% to 100%) compared to 2-tier testing, which detected two false positives for look-alike diseases, providing a specificity of 97% (95% CI, 88% to 100%). For comparison, the sensitivity and specificity for the ELISA first-tier portion of the 2-tier test were calculated to be 75% (95% CI, 57% to 89%) and 77% (95% CI, 64% to 87%), respectively.

Discussion for Examples 9-13

There is an urgent need to develop new tools for improved diagnosis of Lyme disease. Described herein is an example of an objective Lyme disease diagnostic method using iPCR detection of host IgG antibody binding to a single recombinant hybrid antigen.

These data indicate that an iPCR protocol can provide highly consistent and repeatable results across multiple replicates of a single sample. Samples collected from 36 healthy individuals were tested in duplicate for IgM and IgG reactivity using the same antigen to determine the variability of the background across a healthy population. As expected, compared to the within-sample repeatability analysis, observed was a slightly higher standard deviation of the mean Cq values of 0.79 and 0.84 for IgM and IgG, respectively, as well as slightly increased corresponding coefficients of variation of 2.66% and 2.63%, respectively. These data demonstrate that the assay maintains strong repeatability even when compounded with normal human population serum variability. Taken together, these results indicate that the background variability for iPCR detection of host-generated antibodies within and across a healthy human population is well within acceptable levels for the technique.

A panel of eight antigens was generated for use in the iPCR assay. First examined was the level of variability of the background amplification of each antigen across serum samples collected from healthy individuals for both the IgM and IgG isotypes. Each antigen resulted in a unique background amplification mean and standard deviation value for each antigen-isotype combination. This indicated that each antigen-isotype combination performed uniquely using the current iPCR protocol. These data provided the necessary parameters, including the mean background Cq value and the standard deviation of that mean for determining an individual call threshold for each antigen-isotype combination. The call thresholds were established as the mean background Cq value minus a multiple of the standard deviation. The multiplier of standard deviation was unique for each antigen-isotype combination and established based on the minimum multiplier that resulted in no false-positive calls for the CDC research panel I, which served as the training set for optimizing the assay. The ΔCq was calculated as the established threshold call Cq minus the Cq value of the sample. A sample with a ΔCq value of ≥0 was deemed positive by iPCR. Using the panel of eight antigens, this approach duplicated 2-tier testing results with a single early Lyme patient sample (culture positive) testing positive by iPCR that was negative by 2-tier testing. Samples from individuals in the later stages of disease (neurologic and arthritis) tended to test positive for multiple antigens.

In addition to detecting the presence of host antibodies as laboratory support of an exposure to B. burgdorferi, it would be desirable to link an antibody profile with the clinical stage (i.e., early localized, early disseminated with neurological or cardiac involvement, or Lyme arthritis) of illness to better understand disease progression. The results from the human serum panel iPCR testing classified both late Lyme arthritis samples as strongly positive for IgG using the RevA and Crasp2 proteins, with all other categories of samples testing negative for the same two proteins. These results indicate that these two proteins may specifically illicit an immune response in a Lyme arthritis patient as opposed to those in other stages of Lyme disease. According to one embodiment, provided is a method of determining late Lyme associated arthritis involving using the iPCR method to test for and detect RevA and Crasp2 proteins in a biological sample.

The demonstration of iPCR equivalency to 2-tier testing using a panel of antigens demonstrated that the more simplified version of the protocol using a single hybrid antigen was successful. Three antigens known to be seroreactive at different stages of the disease (DbpA, OspC, and VlsE) were synthetically joined by combining the seroreactive peptide portions of OspC and VlsE with the full-length DbpA protein into a single recombinant hybrid antigen termed DOC. The mean background was established for 16 healthy individuals using DOC and showed little variation (standard deviation, 0.57 and 0.51 for anti-*B. burgdorferi* IgM and IgG antibodies, respectively), similar to the results for the full-length antigens tested. The DOC antigen was then used to test CDC research panel I for anti-*B. burgdorferi* IgM and IgG antibodies to establish a positive call threshold. Using the positive call threshold, the DOC iPCR IgG assay demonstrated results equivalent to those for 2-tier testing, with all 2-tier positives identified as positive by iPCR. The quantification of the $\Delta Cq$ for Lyme disease patients showed a trend of increasing average values from early Lyme acute (−1.61) to convalescent early Lyme (0.67) to late-stage Lyme (2.39), suggesting a correlation in the amount of detectable *B. burgdorferi* antibody with disease stage. Interestingly, DOC iPCR IgM was negative for all samples tested, including Lyme disease patient samples. The full-length DbpA antigen alone resulted in a low-positive IgM iPCR value (0.69) for only a single Lyme disease patient sample. iPCR testing using the full-length OspC antigen resulted in a number of IgM iPCR-positive samples, suggesting that the antibodies detected in these samples may have resulted from OspC epitopes other than the PEPC10 sequence. It is also possible that in the context of the DOC hybrid antigen, the PEPC10 sequence lacks the conformational epitope(s) required for IgM recognition. It is well documented that the VlsE antigen primarily generates IgG rather than IgM antibodies early in infection. Therefore, it may not be surprising that the DOC antigen detects IgG antibodies only. These results indicate that testing only the IgG fraction using the DOC hybrid antigen was necessary to achieve a level of sensitivity equivalent to that of 2-tier testing, which required IgM for positive detection in some samples. Given the small sample size, these findings do not rule out the possibility that IgM antibodies might be detected with the DOC iPCR assay in some Lyme disease patient serum samples. Moreover, the additional optimization of the hybrid antigen to include the specific detection of IgM antibodies may contribute to further improved sensitivity for detecting disease in patients with early Lyme disease. Nonetheless, IgM detection has been problematic and controversial due to its contribution to false-positive results and the requirement that IgM testing be used only within the first 4 weeks of infection, suggesting that an assay that does not use IgM may represent an improvement over the current methods of testing for Lyme disease. In addition, the data show that there exists the potential to determine the stage of disease based on the $\Delta Cq$ value of the DOC iPCR assay, which represents another possible improvement over current Lyme disease diagnostics. Accordingly, another embodiment provided herein is a method of determining stage of Lyme disease involving determining the $\Delta Cq$ value of DOC utilizing an iPCR assay. Using $\Delta Cq$ values of known stages of diseases, the $\Delta Cq$ value of DOC in an undetermined biological fluid is tested using iPCR and then stage of disease is determined through correlation with a predetermined $\Delta Cq$ value of DOC for a known disease stage.

iPCR testing of the anti-*B. burgdorferi* IgG antibody fraction using the DOC hybrid antigen was successful at duplicating the 2-tier testing results for a small panel of samples. A larger blinded panel of 92 samples was tested composed of serum samples from Lyme patients (early, early disseminated with cardiac or neurological involvement, and Lyme arthritis), those with look-alike diseases (fibromyalgia, mononucleosis, multiple sclerosis, rheumatoid arthritis, severe periodontitis, and syphilis), and healthy (from areas of endemicity and nonendemicity) individuals (CDC research panel II). iPCR demonstrated 69% sensitivity and 98% specificity compared to 59% and 97%, respectively, for 2-tier testing. A single neurologic Lyme patient tested negative by both iPCR and 2-tier testing. This result is most likely due to the fact that the serum sample was taken 7 days post-erythema migrans (EM), which was likely too early in the infection process to produce an adequate immune response.

It should be borne in mind that all patents, patent applications, patent publications, technical publications, scientific publications, and other references referenced herein and in the accompanying appendices are hereby incorporated by reference in this application to the extent not inconsistent with the teachings herein. In particular, Halpern et al. *Clin Vaccine Immunol* 2014 Aug. 4; 21(8):1094-105 is pertinent to the present disclosure and its teachings are incorporated herein in their entirety.

It is important to an understanding to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding of the invention as disclosed and claimed herein, the following definitions are provided.

While a number of embodiments have been shown and described herein in the present context, such embodiments are provided by way of example only, and not of limitation. Numerous variations, changes and substitutions will occur to those of skilled in the art without materially departing from the invention herein. For example, the present invention need not be limited to best mode disclosed herein, since other applications can equally benefit from the teachings. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

TABLE 1 iPCR DNA oligonucleotide sequences used in this study.

| Oligo number | Oligo ID | SEQ ID NO: | Sequence (5'-3')[a] |
|---|---|---|---|
| T1 | Template 1 (IgG coupled) | 4 | BIOTIN-agcctcagaccaagccagacaactgcctcgtgacgttgctgcc cctaccaacgtacccctacgagtcc |
| T1F | Template 1 Forward | 5 | agcctcagaccaagccagac |
| T1R | Template 1 Reverse | 6 | ggactcgtaggggtacgttgg |
| T1P | Template 1 Probe | 7 | FAM-actgcctcgtgacgttgctgcccct-BHQ1 |
| T2 | Template 2 (IgM coupled) | 8 | BIOTIN-aggaggagggtcaagtcaccaacgctgctccaggccatcgtgct gatctggaccctggatcgagtga |
| T2F | Template 2 Forward | 9 | Aggaggagggtcaagtcacc |
| T2R | Template 2 Reverse | 10 | Tcactcgatccagggtccag |
| T2P | Template 2 Probe | 11 | MAX-acgctgctccaggccatcgtgctga-BHQ1 |
| P1 | OspC partial HA F | 12 | CG GGATCCCATATGtgtaataattcagggaaagatgg |
| P2 | OspC HA R | 13 | ACGCGTCGACttaCGCATAATCCGGCACATCATACGGA-TAaggttttttttgg actttctgc |
| P3 | BmpA partial myc F | 14 | OGGGATCCCATatgtgtagtggtaaaggtagtcttg |
| P4 | BmpA myc R | 15 | ACGCGTCGACttaCAGATCTTCTTCAGAAATAAGTTTTTGT-TCaataaattc tttaagaaacttctcataac |
| P5 | C6 Bb F | 16 | CGGGATCCCATatgaagaaggatgatcagattg |
| P6 | C6 Bb R | 17 | ACGCGTCGACttacttcacagcaaactttccatc |
| P17 | DbpA F | 18 | CGGGATCCggactaacaggagcaacaa |
| P18 | DbpA_PEPC10 R | 19 | AGGITTUTTGGACTTICTGCCACAACAGGgttattttg-catttttcatcag taaaagt |
| P19 | C6_PEPC10 F | 20 | CCTGTTGTGGCAGAAAGTCCAAAAAAACCTatgaagaaggatgatcagat-tgc |
| P20 | C6 Bb R | 21 | ACGCGTCGACttacttcacagcaaactttccatc |

[a]Uppercase letters indicate non-template sequence used for addition of terminal restriction sites andlor epitope tags.

TABLE 2 iPCR DNA oligonucleotides sequences used

| Oligo number | Oligo ID | SEQ ID NO: | Sequence (5'-3')[a] |
|---|---|---|---|
| T1 | Template 1 (IgG coupled) | 22 | BIOTIN-agcctcagaccaagccagacaactgcctcgtgacgttgctgcc cctaccaacgtacccctacgagtcc |
| T1F | Template 1 Forward | 23 | agcctcagaccaagccagac |
| T1R | Template 1 Reverse | 24 | ggactcgtaggggtacgttgg |
| T1P | Template 1 Probe | 25 | FAM-actgcctcgtgacgttgctgccoct-BHQ1 |

TABLE 2 -continued iPCR DNA oligonucleotides sequences used

| Oligo number | Oligo ID | SEQ ID NO: | Sequence (5'-3')[a] |
|---|---|---|---|
| T2 | Template 2 (IgM coupled) | 26 | BIOTIN-aggaggagggtcaagtcaccaacgctgctccaggccatcgtgctgatctggaccctggatcgagtga |
| T2F | Template 2 Forward | 27 | Aggaggagggtcaagtcacc |
| T2R | Template 2 Reverse | 28 | Tcactcgatccagggtccag |
| T2P | Template 2 Probe | 29 | MAX-acgctgctccaggccatcgtgctga-BHQ1 |
| P1 | OspC partial HA F | 30 | CG GGATCCCATATGtgtaataattcagggaaagatgg |
| P2 | OspC HA R | 31 | ACGCGTCGACttaCGCATAATCCGGCACATCATACGGATAaggttttttt ggactttctgc |
| P3 | BmpA partial myc F | 32 | CGGGATCCCATatgtgtagtggtaaaggtagtcttg |
| P4 | BmpA myc R | 33 | ACGCGTCGACttaCAGATCTTCTTCAGAAATAAGTUTTGTTCaataaatt ctttaagaaacttctcataac |
| P5 | C6 Bb F | 34 | CGGGATCCCATatgaagaaggatgatcagattg |
| P6 | C6 Bb R | 35 | ACGCGTCGACttacttcacagcaaactttccatc |
| P17 | DbpA F | 36 | CGGGATCCggactaacaggagcaacaa |
| P18 | DbpA_PEPC10 R | 37 | AGGTTTTTTGGACTTTCTGCCACAACAGGgttattttttgcattttcat cagtaaaagt |
| P19 | C6_PEPC10 F | 38 | CCTGTTGTGGCAGAAAGTCCAAAAAAACCTatgaagaaggatgatcagat-tgc |
| P20 | C6 Bb R | 39 | ACGCGTCGACttacttcacagcaaactttccatc |

[a]Uppercase letters indicate non-template sequence used for addition of terminal restriction sites andlor epitope tags.

TABLE 3 iPCR using DOCigG demonstrates equivalent results to 2-tier testing for a panel of Lyme disease patient sera[a]

| Lyme Disease Stage | Sample Group | Sample ID | Doc IgG[b,c] | IPCR interpretation | 2-Tier Interpretation[d] | Tier1 1 ELISA Interpretation | Tier 2 IgM IB Bands | Tier 2 IgG IB bands |
|---|---|---|---|---|---|---|---|---|
| Stage 1 | Early Lyme-EM | B1 | 2.24 | Pos | Pos | Pos | 41, 39, 23 | 58, 41, 39, 23, 18 |
|  | Early Lyme-EM | B2 | 2.20 | Pos | Pos | Pos | 23 | 66, 45, 41, 39, 23, 18 |
|  | Early Lyme-EM | B3 | 2.07 | Pos | Pos | Pos | 41, 39, 23 | 41, 23 |
|  | Early Lyme-EM | B4 | 2.05 | Pos | Pos | Pos | 41 | 58, 45, 41, 39, 23, 18 |
|  | Early Lyme-EM | B5 | 1.59 | Pos | Pos | Pos | 41, 23 | 41, 23 |
|  | Early Lyme-EM | B6 | 1.45 | Pos | Pos | Pos | 41, 39, 23 | 66, 45, 41, 39, 23, 18 |
|  | Early Lyme-EM | B7 | 1.08 | Pos | Pos | Pos | 41, 39, 23 | 41, 23 |
|  | Early Lyme-EM | B8 | 0.80 | Pos | Pos | Pos | 41, 23 | 41 |
|  | Early Lyme-EM | B9 | 0.52 | Pos | Neg | Pos | 23 | 66, 41, 23 |

TABLE 3-continued iPCR using DOCigG demonstrates equivalent results to 2-tier testing for a panel of Lyme disease patient sera[a]

| Lyme Disease Stage | Sample Group | Sample ID | Doc IgG[b,c] | IPCR interpretation | 2-Tier Interpretation[d] | Tier1 1 ELISA Interpretation | Tier 2 IgM IB Bands | Tier 2 IgG IB bands |
|---|---|---|---|---|---|---|---|---|
| | Early Lyme-EM | B10 | *0.08* | *Pos* | Neg | Equ | — | — |
| | Early Lyme-EM | B11 | (0.08) | Neg | Neg | *Pos* | 23 | 66, 41, 23 |
| | Early Lyme-EM | B12 | (0.27) | Neg | Neg | Neg | — | 66 |
| | Early Lyme-EM | B13 | (0.58) | Neg | Neg | *Pos* | 23 | — |
| | Early Lyme-EM | B14 | (0.91) | Neg | Neg | *Pos* | 23 | 41, 23 |
| | Early Lyme-EM | B15 | (1.00) | Neg | Neg | Neg | — | 67 |
| | Early Lyme-EM | B16 | (1.01) | Neg | Neg | Neg | *39, 23* | 23 |
| | Early Lyme-EM | B17 | (1.22) | Neg | Neg | Neg | — | 23 |
| | Early Lyme-EM | B18 | (1.48) | Neg | Neg | Equ | 23 | 41 |
| | Early Lyme-EM | B19 | (1.50) | Neg | Neg | Neg | 23 | — |
| | Early Lyme-EM | B20 | *1.14* | *Pos* | Neg | *Pos* | 41 | 41, 23, 18 |
| Stage 2 | Neuroborreliosis | B21 | *2.64* | *Pos* | *Pos* | *Pos* | 41, 23 | 45, 41, 23 |
| | Neuroborreliosis | B22 | *2.01* | *Pos* | *Pos* | *Pos* | 41, 39, 23 | 41, 39, 23 |
| | Neuroborreliosis | B23 | *0.00* | *Pos* | *Pos* | *Pos* | 41, 39, 23 | 41, 23 |
| | Neuroborreliosis | B24 | (0.26) | Neg | Neg | Neg | 41, 23 | 41, 23 |
| | Lyme carditis | B25 | *2.83* | *Pos* | *Pos* | *Pos* | 41, 39, 23 | 66, 45, 41, 23, 18 |
| | Lyme carditis | B26 | *1.37* | *Pos* | *Pos* | *Pos* | 41, 39, 23 | 66, 45, 41, 23, 18 |
| Stage 3 | Lyme arthritis | B27 | *3.44* | *Pos* | *Pos* | *Pos* | 23 | 93, 66, 58, 45, 41, 39, 30, 28, 23, 18 |
| | Lyme arthritis | B28 | *2.96* | *Pos* | *Pos* | *Pos* | 41 | 93, 66, 58, 41, 39, 30, 28, 23, 18 |
| | Lyme arthritis | B29 | *2.67* | *Pos* | *Pos* | *Pos* | 41, 23 | 93, 66, 58, 45, 41, 39, 30, 28, 23, 18 |
| | Lyme arthritis | B30 | *2.62* | *Pos* | *Pos* | *Pos* | — | 66, 58, 45, 41, 39, 28, 23, 18 |
| | Lyme arthritis | B31 | *2.09* | *Pos* | *Pos* | *Pos* | 23 | 58, 41, 39, 23, 18 |
| | Lyme arthritis | B32 | *1.84* | *Pos* | *Pos* | *Pos* | — | 93, 66, 58, 41, 39, 30, 23, 18 |
| Non-Lyme | Fibromyalgia | B33 | (0.28) | Neg | Neg | Neg | — | 23 |
| | Fibromyalgia | B34 | (0.81) | Neg | Neg | Neg | 39 | 58, 41 |
| | Fibromyalgia | B35 | (1.70) | Neg | Neg | Neg | — | 41 |
| | Fibromyalgia | B36 | (1.89) | Neg | Neg | Neg | — | 41 |
| | Fibromyalgia | B37 | (1.93) | Neg | Neg | Neg | — | — |
| | Fibromyalgia | B38 | (2.30) | Neg | Neg | Neg | — | — |
| | Rheumatoid arthritis | B39 | (0.90) | Neg | Neg | *Pos* | — | 41 |
| | Rheumatoid arthritis | B40 | (1.17) | Neg | Neg | Neg | — | 41 |

TABLE 3-continued iPCR using DOCigG demonstrates equivalent results to 2-tier testing for a panel of Lyme disease patient sera[a]

| Lyme Disease Stage | Sample Group | Sample ID | Doc IgG[b,c] | IPCR interpretation | 2-Tier Interpretation[d] | Tier1 1 ELISA Interpretation | Tier 2 IgM IB Bands | Tier 2 IgG IB bands |
|---|---|---|---|---|---|---|---|---|
| | Rheumatoid arthritis | B41 | (1.56) | Neg | Neg | Neg | — | — |
| | Rheumatoid arthritis | B42 | (1.73) | Neg | *Pos* | *Pos* | *41, 23* | — |
| | Rheumatoid arthritis | B43 | (1.77) | Neg | Neg | Neg | — | — |
| | Rheumatoid arthritis | B44 | (2.05) | Neg | Neg | Neg | — | — |
| | Multiple sclerosis | B45 | (0.55) | Neg | Neg | Neg | *39, 23* | 41 |
| | Multiple sclerosis | B46 | (0.78) | Neg | Neg | *Pos* | — | 41, 23 |
| | Multiple sclerosis | B47 | (1.09) | Neg | Neg | Neg | — | — |
| | Multiple sclerosis | B48 | (1.11) | Neg | Neg | Neg | 39 | — |
| | Multiple sclerosis | B49 | (1.75) | Neg | Neg | Neg | — | — |
| | Multiple sclerosis | B50 | (2.05) | Neg | Neg | Neg | — | 66 |
| | Mononucleosis | B51 | (0.09) | Neg | Neg | Neg | — | 39 |
| | Mononucleosis | B52 | (0.28) | Neg | Neg | *Pos* | — | 41, 39 |
| | Mononucleosis | B53 | (0.58) | Neg | Neg | *Pos* | — | — |
| | Mononucleosis | B54 | (0.77) | Neg | Neg | Equ | — | 41 |
| | Mononucleosis | B55 | (0.78) | Neg | Neg | Neg | — | — |
| | Mononucleosis | B56 | (1.25) | Neg | Neg | Neg | *41, 23* | 66, 58, 41 |
| | Syphilis | B57 | (0.56) | Neg | Neg | *Pos* | — | — |
| | Syphilis | B58 | (0.75) | Neg | Neg | *Pos* | — | 41 |
| | Syphilis | B59 | (0.96) | Neg | Neg | *Pos* | — | 41 |
| | Syphilis | B60 | (1.01) | Neg | *Pos* | *Pos* | *39, 23* | — |
| | Syphilis | B61 | (1.38) | Neg | Neg | *Pos* | — | 41 |
| | Syphilis | B62 | (1.47) | Neg | Neg | Neg | — | — |
| | Severe Periodontitis | B63 | (0.22) | Neg | Neg | Neg | — | — |
| | Severe Periodontitis | B64 | (0.29) | Neg | Neg | Neg | — | — |
| | Severe Periodontitis | B65 | (0.56) | Neg | Neg | Neg | — | — |
| | Severe Periodontitis | B66 | (0.90) | Neg | Neg | Neg | — | 45, 41 |
| | Severe Periodontitis | B67 | (1.03) | Neg | Neg | Neg | — | 66 |
| | Severe Periodontitis | B68 | (3.04) | Neg | Neg | Neg | — | — |
| Healthy | Healthy endemic | B69 | 0.23 | *Pos* | Neg | Neg | — | 23 |
| | Healthy endemic | B70 | (0.04) | Neg | Neg | *Pos* | 41 | 66 |
| | Healthy endemic | B71 | (0.53) | Neg | Neg | *Pos* | — | 41, 23 |
| | Healthy endemic | B72 | (0.87) | Neg | Neg | Neg | 23 | 41 |
| | Healthy endemic | B73 | (0.87) | Neg | Neg | Equ | 23 | — |
| | Healthy endemic | B74 | (1.11) | Neg | Neg | Neg | — | 45,41 |
| | Healthy endemic | B75 | (1.16) | Neg | Neg | Neg | — | — |
| | Healthy endemic | B76 | (1.37) | Neg | Neg | Neg | — | — |
| | Healthy endemic | B77 | (1.42) | Neg | Neg | Neg | — | — |
| | Healthy endemic | B78 | (1.49) | Neg | Neg | Neg | — | 66, 41 |
| | Healthy endemic | B79 | (1.95) | Neg | Neg | Neg | 23 | — |
| | Healthy endemic | B80 | (2.47) | Neg | Neg | *Pos* | 23 | 58, 41, 39, 18 |
| | Healthy non-endemic | B81 | (0.53) | Neg | Neg | Neg | — | 41 |

TABLE 3-continued iPCR using DOCigG demonstrates equivalent results to 2-tier testing for a panel of Lyme disease patient sera[a]

| Lyme Disease Stage | Sample Group | Sample ID | Doc IgG[b,c] | IPCR interpretation | 2-Tier Interpretation[d] | Tier1 1 ELISA Interpretation | Tier 2 IgM IB Bands | Tier 2 IgG IB bands |
|---|---|---|---|---|---|---|---|---|
| | Healthy non-endemic | B82 | (0.60) | Neg | Neg | Neg | *41, 23* | 41 |
| | Healthy non-endemic | B83 | (0.78) | Neg | Neg | Equ | — | — |
| | Healthy non-endemic | B84 | (0.80) | Neg | Neg | | — | — |
| | Healthy non-endemic | B85 | (0.86) | Neg | Neg | Neg | — | — |
| | Healthy non-endemic | B86 | (0.90) | Neg | Neg | Neg | — | 58, 45 |
| | Healthy non-endemic | B87 | (1.09) | Neg | Neg | Neg | — | 66, 58, 45, 41 |
| | Healthy non-endemic | B88 | (1.15) | Neg | Neg | Neg | — | 41 |
| | Healthy non-endemic | B89 | (1.17) | Neg | Neg | Neg | — | 41 |
| | Healthy non-endemic | B90 | (1.77) | Neg | Neg | Neg | 23 | — |
| | Healthy non-endemic | B91 | (2.06) | Neg | Neg | Neg | 23 | — |
| | Healthy non-endemic | B92 | (2.09) | Neg | Neg | Neg | — | — |

[a]italicized boxes indicate positive assay result/interpretation.
[b]Values shown represent a ΔCq in reference to the antigen/isotype background threshold Cq value determined using an antigen specific multiplier of the SD above the mean value for a set of healthy individuals for each antigen/isotype combination, as described in the Material and Methods.
[c]Values in parenthesis represent negative iPCR ΔCq values.
[d]2-tier results established by standard ELISA and IgG/IgM immunoblot (IB) protocols.
[e]EM, erythema migrans

What is claimed is:

1. A method of detecting a *Borrelia* species infection marker in a human or non-human mammal subject, the method comprising: exposing a biological sample from the subject to a capture substrate comprising a recombinant antigen that comprises a fusion protein of SEQ ID NO: 1 under conditions for an infection marker in said biological sample to associate with the capture substrate to form a capture complex; associating said capture complex with a marker complex, said marker complex comprising an oligonucleotide; amplifying said oligonucleotide of marker complex associated with said capture complex to produce an amplification signal and detecting presence of the infection marker in the sample based on if the amplification signal is above a predetermined threshold.

2. The method of claim 1 wherein said capture substrate comprises a solid support with the fusion protein bound thereto.

3. The method of claim 2, wherein said solid support is a bead.

4. The method of claim 1, wherein said *Borrelia* species is *Borrelia burgdorferi, Borrelia afzelli* and/or *Borrelia garinii*.

5. The method of claim 1, wherein said at least one recombinant antigen is produced with a tag that is subsequently cleaved.

6. The method of claim 5, wherein said tag is a glutathione-S-transferase (GST) tag, a hemagglutinin, or C-Myc, or combinations thereof.

7. The method of claim 1, wherein said infection marker is a primary host antibody that binds to a Lyme disease *Borrelia* species or a Lyme disease *Borrelia* epitope comprising antigen.

8. The method of claim 1, wherein the amplification signal is fluorescence.

9. The method of claim 8, wherein the predetermined signal threshold is greater than or equal to three standard deviations above a mean background signal.

* * * * *

SEQUENCE LISTING

<160> NUMBER OF SEQ ID NOS: 39

<210> SEQ ID NO 1
<211> LENGTH: 226
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

Met Ile Lys Cys Asn Asn Lys Thr Phe Asn Asn Leu Leu Lys Leu Thr
1               5                   10                  15

Ile Leu Val Asn Leu Leu Ile Ser Cys Gly Leu Thr Gly Ala Thr Lys
            20                  25                  30

Ile Arg Leu Glu Arg Ser Ala Lys Asp Ile Thr Asp Glu Ile Asp Ala
        35                  40                  45

Ile Lys Lys Asp Ala Ala Leu Lys Gly Val Asn Phe Asp Ala Phe Lys
    50                  55                  60

Asp Lys Lys Thr Gly Ser Gly Val Ser Glu Asn Pro Phe Ile Leu Glu
65                  70                  75                  80

Ala Lys Val Arg Ala Thr Thr Val Ala Glu Lys Phe Val Ile Ala Ile
                85                  90                  95

Glu Glu Glu Ala Thr Lys Leu Lys Glu Thr Gly Ser Ser Gly Glu Phe
            100                 105                 110

Ser Ala Met Tyr Asp Leu Met Phe Glu Val Ser Lys Pro Leu Gln Lys
        115                 120                 125

Leu Gly Ile Gln Glu Met Thr Lys Thr Val Ser Asp Ala Ala Glu Glu

```
                    130                 135                 140
Asn Pro Pro Thr Thr Ala Gln Gly Val Leu Glu Ile Ala Lys Lys Met
145                 150                 155                 160

Arg Glu Lys Leu Gln Arg Val His Thr Lys Asn Tyr Cys Thr Leu Lys
                165                 170                 175

Lys Lys Glu Asn Ser Thr Phe Thr Asp Glu Lys Cys Lys Asn Asn Pro
            180                 185                 190

Val Val Ala Glu Ser Pro Lys Lys Pro Met Lys Lys Asp Asp Gln Ile
        195                 200                 205

Ala Ala Ala Ile Ala Leu Arg Gly Met Ala Lys Asp Gly Lys Phe Ala
    210                 215                 220

Val Lys
225

<210> SEQ ID NO 2
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Lys Lys Tyr Ile Ile Asn Leu Ser Leu Cys Leu Leu Leu Leu Ser
1               5                   10                  15

Cys Asn Leu Phe Ser Lys Asp Ser Arg Ser Arg Gln Lys Tyr Asn Phe
                20                  25                  30

Lys Val Pro Ala Lys Ser Val Ser Asn Pro Ile Asn Lys Glu Asn Ile
            35                  40                  45

Asp Thr Glu Lys Gly Thr Asn Thr Thr Leu Cys Ile Lys Glu Lys Asp
        50                  55                  60

Ser Arg Ile Ile Ile Lys Asp Cys Ile Asn Asn Gln Glu Leu Phe Lys
65                  70                  75                  80

Val Lys Ser Lys Arg Arg Tyr Asp Phe Lys Lys Ala Met Leu Leu Gly
                85                  90                  95

Ile Gln Thr Ala Leu Lys Val Ile Asn Ile Gly Asn Asn Asn Lys Lys
            100                 105                 110

Leu Thr Ser Ile Lys Lys His Asn Asp His Ile Leu Leu Glu Phe Lys
        115                 120                 125

Asp Asn Lys Ile Tyr Ile Ile Arg Leu Ser Glu Leu Lys Lys His Leu
    130                 135                 140

Leu Lys Ser Lys Lys Lys Pro Leu Leu Gly Ser Pro Ile Pro Gly Gly
145                 150                 155                 160

Gly Asp Ala Glu Phe Val Asp Asp Pro Asp Gly Arg Ile Glu Ala Glu
                165                 170                 175

Leu Glu Ala Glu Gln Glu Gln Glu Met Leu Asp Arg Glu Asp Phe Gly
            180                 185                 190

Asp Glu Glu Asp Glu Glu Leu Glu Glu Ile Phe Gly Lys Glu Lys
        195                 200                 205

Pro Asn Asn
    210

<210> SEQ ID NO 3
<211> LENGTH: 330
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 3

Leu Ile Ile Lys Val Met Leu Ile Ser Ser Leu Phe Ser Ser Phe Ile
1               5                   10                  15

Ser Cys Lys Leu Tyr Glu Lys Leu Thr Asn Lys Ser Gln Gln Ala Leu
            20                  25                  30

Ala Lys Ala Phe Val Tyr Asp Lys Asp Ile Ala Asp Asn Lys Ser Thr
        35                  40                  45

Asn Ser Thr Ser Lys Leu Asp Asn Ser Ser Leu Asp Ser Ile Lys Asp
    50                  55                  60

Asn Asn Arg Ser Gly Arg Thr Ser Lys Ala Leu Asp Asp Ala Glu Glu
65                  70                  75                  80

Ile Gly Val Lys Glu Ser Asn Gln Asn Arg Asn Asp Gln Gln Asn
                85                  90                  95

Asn Glu Ser Lys Val Lys Glu Ser Gly Lys Asn Asn Ser Ser Gly Ile
                100                 105                 110

Gln Ala Asp Asp Ser Val Leu Asp Thr Ala His Ser Asp Ala Ser Glu
            115                 120                 125

Val Glu Asn Lys Lys His Asp Thr Ser Arg Gln Pro Gln Leu Leu Asn
130                 135                 140

Lys Asp Ser Ser Glu Ala Arg Glu Ala Ser Lys Ile Ile Gln Lys Ala
145                 150                 155                 160

Ser Thr Ser Leu Glu Glu Ala Glu Lys Val Asn Ala Ala Leu Lys Glu
                165                 170                 175

Thr Arg Ser Lys Leu Asp Lys Ile Lys Arg Leu Ala Asp Ser Ala Lys
            180                 185                 190

Ser Tyr Leu Asn Asn Ala Arg Lys Asn Ser Arg Thr Asn Gly Ser Ile
        195                 200                 205

Leu Glu Ile Leu Pro Asn Leu Asp Lys Ala Ile Glu Lys Ala Ile Ser
    210                 215                 220

Ser Tyr Ala Ser Leu Asn Val Cys Tyr Thr Asp Ala Ile Ala Ala Leu
225                 230                 235                 240

Ala Lys Ala Lys Asn Asp Phe Glu His Ala Lys Arg Lys Ala Asn Asp
                245                 250                 255

Ala Leu Glu Glu Ala Leu Lys Asp Ile Pro His Phe Arg Gly Tyr Asn
            260                 265                 270

Tyr Leu Tyr His Tyr Arg Ile Asn Asn Ala Asn Asp Ala Met Glu Ser
        275                 280                 285

Ala Lys Ser Leu Leu Glu Val Ala Lys Asn Lys Gln Lys Glu Leu Asn
    290                 295                 300

Glu Asn Met Thr Lys Thr Asn Lys Asp Phe Gln Glu Leu Asn Asp Ile
305                 310                 315                 320

Tyr Lys Lys Leu Gln Asp Met Asp Ser Arg
                325                 330

<210> SEQ ID NO 4
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4

```
agcctcagac caagccagac aactgcctcg tgacgttgct gcccctacca acgtacccct    60
acgagtcc                                                              68
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

```
agcctcagac caagccagac                                                 20
```

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6

```
ggactcgtag gggtacgttg g                                               21
```

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7

```
actgcctcgt gacgttgctg cccct                                           25
```

<210> SEQ ID NO 8
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8

```
aggaggaggg tcaagtcacc aacgctgctc caggccatcg tgctgatctg gaccctggat    60
cgagtga                                                               67
```

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

```
aggaggaggg tcaagtcacc                                                 20
```

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tcactcgatc cagggtccag                                              20

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
acgctgctcc aggccatcgt gctga                                        25

<210> SEQ ID NO 12
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cgggatccca tatgtgtaat aattcaggga aagatgg                           37

<210> SEQ ID NO 13
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
acgcgtcgac ttacgcataa tccggcacat catacggata aggttttttt ggactttctg  60
c                                                                  61

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cgggatccca tatgtgtagt ggtaaaggta gtcttg                            36

<210> SEQ ID NO 15
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
acgcgtcgac ttacagatct tcttcagaaa taagtttttg ttcaataaat tctttaagaa  60
acttctcata ac                                                      72

<210> SEQ ID NO 16
<211> LENGTH: 33
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 16
cgggatccca tatgaagaag gatgatcaga ttg                                    33

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
acgcgtcgac ttacttcaca gcaaactttc catc                                   34

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cgggatccgg actaacagga gcaacaa                                           27

<210> SEQ ID NO 19
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
aggttttttt ggactttctg ccacaacagg gttatttttg cattttcat cagtaaaagt       60

<210> SEQ ID NO 20
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cctgttgtgg cagaaagtcc aaaaaaacct atgaagaagg atgatcagat tgc             53

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
acgcgtcgac ttacttcaca gcaaactttc catc                                   34

<210> SEQ ID NO 22
<211> LENGTH: 68
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 22
agcctcagac caagccagac aactgcctcg tgacgttgct gcccctacca acgtacccct    60
acgagtcc                                                             68

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
agcctcagac caagccagac                                                20

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ggactcgtag gggtacgttg g                                              21

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
actgcctcgt gacgttgctg cccct                                          25

<210> SEQ ID NO 26
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
aggaggaggg tcaagtcacc aacgctgctc caggccatcg tgctgatctg gaccctggat    60
cgagtga                                                              67

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
aggaggaggg tcaagtcacc                                                20

<210> SEQ ID NO 28
<211> LENGTH: 20

-continued

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tcactcgatc cagggtccag                                                    20

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
acgctgctcc aggccatcgt gctga                                              25

<210> SEQ ID NO 30
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cgggatccca tatgtgtaat aattcaggga aagatgg                                 37

<210> SEQ ID NO 31
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
acgcgtcgac ttacgcataa tccggcacat catacggata aggttttttt ggactttctg        60
c                                                                        61

<210> SEQ ID NO 32
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
cgggatccca tatgtgtagt ggtaaaggta gtcttg                                  36

<210> SEQ ID NO 33
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
acgcgtcgac ttacagatct tcttcagaaa taagtttttg ttcaataaat tctttaagaa        60
acttctcata ac                                                            72

<210> SEQ ID NO 34
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
cgggatccca tatgaagaag gatgatcaga ttg                               33

<210> SEQ ID NO 35
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
acgcgtcgac ttacttcaca gcaaactttc catc                              34

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cgggatccgg actaacagga gcaacaa                                      27

<210> SEQ ID NO 37
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
aggttttttt ggactttctg ccacaacagg gttattttg catttttcat cagtaaaagt   60

<210> SEQ ID NO 38
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
cctgttgtgg cagaaagtcc aaaaaaacct atgaagaagg atgatcagat tgc         53

<210> SEQ ID NO 39
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
acgcgtcgac ttacttcaca gcaaactttc catc                              34